US007314725B2

(12) United States Patent
Drayna et al.

(10) Patent No.: US 7,314,725 B2
(45) Date of Patent: Jan. 1, 2008

(54) PHENYLTHIOCARBAMIDE (PTC) TASTE RECEPTOR

(75) Inventors: Dennis Drayna, Potomac, MD (US); Un-Kyung Kim, Gaithersburg, MD (US); Mark Leppert, Salt Lake City, UT (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 534 days.

(21) Appl. No.: 10/484,525

(22) PCT Filed: Jul. 19, 2002

(86) PCT No.: PCT/US02/23172

§ 371 (c)(1),
(2), (4) Date: Jan. 20, 2004

(87) PCT Pub. No.: WO03/008627

PCT Pub. Date: Jan. 30, 2003

(65) Prior Publication Data

US 2004/0248123 A1    Dec. 9, 2004

Related U.S. Application Data

(60) Provisional application No. 60/306,991, filed on Jul. 20, 2001.

(51) Int. Cl.
*C07K 14/705* (2006.01)
*C12N 15/12* (2006.01)
*G01N 33/566* (2006.01)

(52) U.S. Cl. .................. 435/7.21; 435/69.1; 435/69.7; 435/252.3; 435/320.1; 530/350; 536/23.4; 536/23.5

(58) Field of Classification Search ..................... None
See application file for complete search history.

(56) References Cited

U.S. PATENT DOCUMENTS

| 5,380,765 | A | 1/1995 | Hirsch |
| 5,972,621 | A | 10/1999 | Tartaglia et al. |
| 6,159,700 | A | 12/2000 | Aiyar et al. |
| 6,383,778 | B1 | 5/2002 | Zuker et al. |
| 6,540,978 | B1 | 4/2003 | Margolskee et al. |
| 6,558,910 | B2 | 5/2003 | Zuker et al. |
| 2002/0048763 | A1 | 4/2002 | Penn et al. |
| 2002/0094551 | A1 | 7/2002 | Adler et al. |
| 2002/0128433 | A1 | 9/2002 | Yao et al. |
| 2003/0022278 | A1 | 1/2003 | Zuker et al. |
| 2003/0143668 | A1 | 7/2003 | Suwa et al. |
| 2003/0235833 | A1 | 12/2003 | Suwa et al. |

FOREIGN PATENT DOCUMENTS

| CA | 2418130 | 2/2003 |
| EP | 1270724 | 1/2003 |
| WO | WO 99/06830 | 2/1999 |
| WO | WO 99/64626 | 12/1999 |
| WO | WO 00/38536 | 7/2000 |
| WO | WO 01/18050 | 3/2001 |
| WO | WO 01/66563 | 9/2001 |
| WO | WO 01/77676 | 10/2001 |
| WO | WO 01/77676 A1 | 10/2001 |
| WO | WO 02/16548 | 2/2002 |
| WO | WO 02/36622 | 5/2002 |
| WO | WO 02/068579 | 9/2002 |
| WO | WO 02/103005 | 12/2002 |
| WO | WO 03/006482 | 1/2003 |
| WO | WO 2004/029087 | 4/2004 |
| WO | WO 2005/007891 | 1/2005 |

OTHER PUBLICATIONS

Anne-Spence et al., "Estimating the Recombination frequency for the PTC—Kell linkage," *Hum Genet* 67: 183-186, 1984.
Bufe et al., "The human TAS2R16 receptor mediates bitter taste in response to β- glucopyranosides," *Nature Genetics* 32: 397-401, 2002.
Chandrashekar et al., "T2Rs Function as Bitter Taste Receptors," *Cell* 100: 703-711, 2000.
Conte et al., "Identification and characterization of human taste receptor genes belonging to the TAS2R family," *Cytogenet Genome Res* 98: 45-53, 2002.
Drayna, et al., "Genetic analysis of a complex trait in the Utah Genetic Reference Project: a major locus for PTC taste ability on chromosome 7q and a secondary locus on chromosome 16p," *Hum. Genet.* 112: 567-572, 2003.
Gillis, "Genetics May Hold Clues to Smell, Taste," *Los Angeles Times*, Jun. 4, 2001.
Guo and Reed, "The genetics of phenylthiocarbamide perception," *Annals of Huamn Biology* 28(2): 111-142, 2001.
Kim et al., "Positional Cloning of the Human Quantitative Trait Locus Underlying Taste Sensitivity to Phenylthiocarbamide," *Science* 299: 1221-1225, 2003.
Matsunami et al., "A family of candidate taste receptors in human and mouse," *Nature* 404: 601-604, 2000.
McLaughlin et al., "Gustducin is a taste-cell-specific G protein closely related to the transducins," *Nature* 357: 563-569, 1992.
Miyajima et al., "Expression of murine and human granulocyte-macrophage colony-stimulating factors in *S. cerevisiae*: mutagenesis of the potential glycosylation sites," *EMBO J* 5: 1193-1197, 1986.
Offermans and Simon, "Gα15 and Gα16 couple a wide variety of receptors to phospholipase C," *J. Biol. Chem.* 270: 15175-15180, 1995.
Shi et al, "Adaptive Diversification of Bitter Taste Receptor Genes in Mammalian Evolution," *Mol. Biol. Evol.* 20:805-814, 2003.
Sulston and Waterston, "Toward a complete human genome sequence," *Genome Research* 8: 1097-1108, 1998.

(Continued)

*Primary Examiner*—John Ulm
(74) *Attorney, Agent, or Firm*—Klarquist Sparkman LLP

(57) ABSTRACT

The invention provides isolated nucleic and amino acid sequences of a taste cell receptor that serves as a sensor for the bitter taste of phenylthiocarbamide (PTC), antibodies to such PTC taste receptor, methods of detecting such nucleic and amino acid sequences, and methods of screening for modulators of such PTC taste receptor.

24 Claims, 8 Drawing Sheets

OTHER PUBLICATIONS

Vaidehi et al., "Prediction of structure and function of G protein-coupled receptors," *PNAS 99*: 12622-12627, 2002.

Wooding et al., "Natural Selection and Molecular Evolution in PTC, a Bitter—Taste Receptor Gene," *Am. J. Genet.* 74:_, 2004 (10 pages).

DNA Sequence: "*Homo sapiens* BAC clone RP11-707F14 from 7, complete sequence," Accession No. AC073647 (30 pages).

DNA Sequence: "*Homo sapiens* taste receptor, type 2, member 38 (TAS2R38), mRNA," Accession No. NM 176817 (2 pages).

DNA Sequence: "Novel G-protein coupled receptors," Accession No. BD144608 (1 page).

Bufe, "Dissertation zur Erlangung des Doktorgrades an der Universitat Potsdam: Identifizierung and Charakterisierung von Bitterezeptoren," http://www.pub.ub.uni-potsdam.de/2004/0013/bufe.pdf, (May 2003).

Lipshutz et al.. "High density synthetic oligonucleotide arrays," *Nature Genetics Suppl* 21:20-24, (Jan. 1999).

Ueda et al., "Identification of coding single—nucleotide polymorphisms in human taste receptor genes involving bitter tasting," *Biochem and Biophys Research Communications* 285(1):147-151, (Jul. 6, 2001).

DBSNP Database Accession No. RS2234233; Genaissance: ss3181754 *NCI*, (Jul. 19, 2001).

DBSNP Database Accession No. SS27118533; TSC-CSHL: submitted SNP details, *NBCI*, (Jan. 2, 2001).

DBSNP Database Accession No. RS41469; TSC-CSHL: ss2718533, *NBCI*, (Jan. 2, 2001).

DBSNP Database Accession No. RS597468; refSNP ID: rs597468, *NBCI*, (Jul. 27, 2000).

DBSNP Database Accession No. RS2692396; C/G SNP at AA 101 of T2R16, *NBCI*, (Sep. 25, 2001).

DBSNP Database Accession No. RS2233988, *NBCI*, (Jul. 19, 2001).

DBSNP Database Accession No. RS2233989, *NBCI*, (Jul. 19, 2001).

DBSNP Database Accession No. RS846664, *NBCI*, (Sep. 2, 2000).

DBSNP Database Accession No. RS860170, *NBCI*, (Sep. 2, 2000).

DBSNP Database Accession No. RS1204014, *NBCI*, (Oct. 5, 2000).

Geneseq Database Accession No. GNS:AAD05499, "Human secreted protein—encoding gene 8 cDNA clone HBBBC71, Seq. ID No. 18", *EBI*, (Jul. 18, 2001).

EBML Database Accession No. EM_PRO:AF494228, "*Homo sapiens* candidate taste receptor TAS2R44 gene, complete cds", *EBI*, (Apr. 29, 2002).

EBML Database Accession No. EM_PRO:AF494237, "*Homo sapiens* candidate taste receptor TAS2R43 gene, complete cds", *EBI*, (Apr. 29, 2002).

EBML Database Accession No. EM_PRO:AF494236, "*Homo sapiens* candidate taste receptor TAS2R49 gene, complete cds", *EBI*, (Apr. 29, 2002).

Alder et al., "A novel family of mammalian taste receptors," *Cell*, 100:693-702, 2000.

Hoon M.A. et al., "Putative Mammalian Taste Receptors: A Class of taste-specific GPCRS with distinct topograhic selectivity," *Cell*, 96:541-551, 1999.

Kim U-K et al., "Positional cloning of the human quantitative trait locus underlying taste sensitivity trait locus underlying taste sensitivity to phenylthiocarbamide," *Science*, 299:1221-1225, 2003.

Reed D. R. et al., "Localization of a gene for bitter—taste perception human chromosome 5p15," *American J. of Human Genetics*, 64:1478-1480, 1999.

Guo and Reed, "The genetics of phenylthiocarbamide perception," *Annals of Human Biology* 28(2): 111-142, 2001.

Kim et al., "Positional Cloning of the Human Quantitative Trait Locus Underlying Taste Sensitivity to Phenylthiocarbamide," *Science* 299: 1221-1225, 2003.

Matsunami et al., "A family of candidate taste receptors in human and mouse," *Nature* 404: 601-604, 2000.

McLaughlin et al., "Gustducin is a taste-cell-specific G protein closely related to the transducins," *Nature* 357: 563-569, 1992.

Miyajima et al., "Expression of murine and human granulocyte-macrophage colony—stimulating factors in *S. cerevisiae*: mutagenesis of the potential glycosylation sites," *EMBO J* 5: 1193-1197, 1986.

Offermans and Simon, "Gα15 and Gα16 couple a wide variety of receptors to phospholipase C," *J. Biol. Chem.* 270: 15175-15180, 1995.

Shi et al, "Adaptive Diversification of Bitter Taste Receptor Genes in Mammalian Evolution," *Mol. Biol. Evol.* 20:805-814, 2003.

Sulston and Waterston, "Toward a complete human genome sequence," *Genome Research* 8: 1097-1108, 1998.

Vaidehi et al., "Prediction of structure and function of G protein-coupled receptors," *PNAS 99*: 12622-12627, 2002.

Wooding et al., "Natural Selection and Molecular Evolution in PTC, a Bitter-Taste Receptor Gene," *Am. J. Genet.* 74:_-_, 2004 (10 pages).

DNA Sequence: "*Homo sapiens* BAC clone RP11-707F14 from 7, complete sequence," Accession No. AC073647 (30 pages), Jan. 31, 2004.

DNA Sequence: "*Homo sapiens* taste receptor, type 2, member 38 (TAS2R38), mRNA," Accession No. NM_176817 (2 pages), Dec. 22, 2003.

DNA Sequence: "Novel G-protein coupled receptors," Accession No. BD144608 (1 page), Jan. 17, 2003.

Figure 1

PTC gene (1002bp, 333 aa)

```
     atgttgactctaactcgcatccgcactgtgtcctatgaagtcagg
  1  M  L  T  L  T  R  I  R  T  V  S  Y  E  V  R     15
     agtacatttctgttcatttcagtcctggagtttgcagtggggttt
 16  S  T  F  L  F  I  S  V  L  E  F  A  V  G  F     30
     ctgaccaatgccttcgtttcttggtgaattttgggatgtagtg
 31  L  T  N  A  F  V  F  L  V  N  F  W  D  V  V     45
     aagaggcagccactgagcaacagtgattgtgtgctgctgtgtctc
 46  K  R  Q  P  L  S  N  S  D  C  V  L  C  L       60
     agcatcagccggcttttcctgcatggactgctgttcctgagtgct
 61  S  I  S  R  L  F  L  H  G  L  L  F  L  S  A     75
     atccagcttacccacttccagaagttgagtgaaccactgaaccac
 76  I  Q  L  T  H  F  Q  K  L  S  E  P  L  N  H     90
     agctaccaagccatcatcatgctatggatgattgcaaaccaagcc
 91  S  Y  Q  A  I  I  M  L  W  M  I  A  N  Q  A    105
     aacctctggcttgctgcctgcctcagcctgctttactgctccaag
106  N  L  W  L  A  A  C  L  S  L  L  Y  C  S  K    120
     ctcatccgtttctctcacaccttcctgatctgcttggcaagctgg
121  L  I  R  F  S  H  T  F  L  I  C  L  A  S  W    135
     gtctccaggaagatctcccagatgctcctgggtattattctttgc
136  V  S  R  K  I  S  Q  M  L  L  G  I  I  L  C    150
     tcctgcatctgcactgtcctctgtgtttggtgcttttttagcaga
151  S  C  I  C  T  V  L  C  V  W  C  F  F  S  R    165
     cctcacttcacagtcacaactgtgctattcatgaataacaataca
166  P  H  F  T  V  T  T  V  L  F  M  N  N  N  T    180
     aggctcaactggcagattaaagatctcaatttattttattcctttt
181  R  L  N  W  Q  I  K  D  L  N  L  F  Y  S  F    195
     ctcttctgctatctgtggtctgtgcctcctttcctattgtttctg
196  L  F  C  Y  L  W  S  V  P  P  F  L  L  F  L    210
     gtttcttctgggatgctgactgtctccctgggaaggcacatgagg
211  V  S  S  G  M  L  T  V  S  L  G  R  H  M  R    225
     acaatgaaggtctataccagaaactctcgtgaccccagcctggag
226  T  M  K  V  Y  T  R  N  S  R  D  P  S  L  E    240
     gcccacattaaagccctcaagtctcttgtctcctttttctgcttc
241  A  H  I  K  A  L  K  S  L  V  S  F  F  C  F    255
     tttgtgatatcatcctgtgctgccttcatctctgtgcccctactg
256  F  V  I  S  S  C  A  A  F  I  S  V  P  L  L    270
     attctgtggcgcgacaaaatagggtgatggtttgtgttgggata
271  I  L  W  R  D  K  I  G  V  M  V  C  V  G  I    285
     atggcagcttgtccctctgggcatgcagccatcctgatctcaggc
286  M  A  A  C  P  S  G  H  A  A  I  L  I  S  G    300
     aatgccaagttgaggagagctgtgatgaccattctgctctgggct
301  N  A  K  L  R  R  A  V  M  T  I  L  L  W  A    315
     cagagcagcctgaaggtaagagccgaccacaaggcagattcccgg
316  Q  S  S  L  K  V  R  A  D  H  K  A  D  S  R    330
     acactgtgctga
331  T  L  C  *                                     333
```

Genetic variation : GCA (Ala) → CCA (Pro) at 49
[Non-taster]    [Taster]

Figure 2

PTC gene (1002bp, 333 aa)

```
         atgttgactctaactcgcatccgcactgtgtcctatgaagtcagg
  1      M  L  T  L  T  R  I  R  T  V  S  Y  E  V  R    15
         agtacatttctgttcatttcagtcctggagtttgcagtggggttt
 16      S  T  F  L  F  I  S  V  L  E  F  A  V  G  F    30
         ctgaccaatgccttcgttttcttggtgaattttgggatgtagtg
 31      L  T  N  A  F  V  F  L  V  N  F  W  D  V  V    45
         aagaggcaggcactgagcaacagtgattgtgtgctgctgtgtctc
 46      K  R  Q  A  L  S  N  S  D  C  V  L  L  C  L    60
         agcatcagccggcttttcctgcatggactgctgttcctgagtgct
 61      S  I  S  R  L  F  L  H  G  L  L  F  L  S  A    75
         atccagcttacccacttccagaagttgagtgaaccactgaaccac
 76      I  Q  L  T  H  F  Q  K  L  S  E  P  L  N  H    90
         agctaccaagccatcatcatgctatggatgattgcaaaccaagcc
 91      S  Y  Q  A  I  I  M  L  W  M  I  A  N  Q  A   105
         aacctctggcttgctgcctgcctcagcctgctttactgctccaag
106      N  L  W  L  A  A  C  L  S  L  L  Y  C  S  K   120
         ctcatccgtttctctcacaccttcctgatctgcttggcaagctgg
121      L  I  R  F  S  H  T  F  L  I  C  L  A  S  W   135
         gtctccaggaagatctcccagatgctcctgggtattattctttgc
136      V  S  R  K  I  S  Q  M  L  L  G  I  I  L  C   150
         tcctgcatctgcactgtcctctgtgtttggtgcttttttagcaga
151      S  C  I  C  T  V  L  C  V  W  C  F  F  S  R   165
         cctcacttcacagtcacaactgtgctattcatgaataacaataca
166      P  H  F  T  V  T  T  V  L  F  M  N  N  N  T   180
         aggctcaactggcagattaaagatctcaatttatttattccttt
181      R  L  N  W  Q  I  K  D  L  N  L  F  Y  S  F   195
         ctcttctgctatctgtggtctgtgcctcctttcctattgtttctg
196      L  F  C  Y  L  W  S  V  P  P  F  L  L  F  L   210
         gtttcttctgggatgctgactgtctccctgggaaggcacatgagg
211      V  S  S  G  M  L  T  V  S  L  G  R  H  M  R   225
         acaatgaaggtctataccagaaactctcgtgaccccagcctggag
226      T  M  K  V  Y  T  R  N  S  R  D  P  S  L  E   240
         gcccacattaaagccctcaagtctcttgtctccttttctgcttc
241      A  H  I  K  A  L  K  S  L  V  S  F  F  C  F   255
         tttgtgatatcatcctgtgctgccttcatctctgtgcccctactg
256      F  V  I  S  S  C  A  A  F  I  S  V  P  L  L   270
         attctgtggcgcgacaaaatagggggtgatggtttgtgttgggata
271      I  L  W  R  D  K  I  G  V  M  V  C  V  G  I   285
         atggcagcttgtccctctgggcatgcagccatcctgatctcaggc
286      M  A  A  C  P  S  G  H  A  A  I  L  I  S  G   300
         aatgccaagttgaggagagctgtgatgaccattctgctctgggct
301      N  A  K  L  R  R  A  V  M  T  I  L  L  W  A   315
         cagagcagcctgaaggtaagagccgaccacaaggcagattccgg
316      Q  S  S  L  K  V  R  A  D  H  K  A  D  S  R   330
         acactgtgctga
331      T  L  C  *                                    333
```

Genetic variation : GCA (Ala) → CCA (Pro) at 49
                    [Non-taster]    [Taster]

CLUSTAL W multiple sequence alignment                          Figure 4

```
             1                                                          60
PTCgene_     MLTLTRIRTVSYEVRSTFLFISVLEFAVGFLTNAFVFLVNFWDVVKRQALSNSDCVLLCL
   hT2R1_    MLESHLI---------IYFLLAVIQFLLGIFTNGIIVVVNGIDLIKHRKMAPLDLLLLSCL
   rT2R1_    MMEGHIL---------FFFLVVMVQFVTGVLANGLIVVVHAIDLIMWKKMAPLDLLLLFCL
  mT2R19_    MMEGHML---------FFLLVVVVQFLTGVLANGLIVVVNAIDLIMWKKMAPLDLLLLFCL
   hT2R3_    MMGLTEG---------VFLILSGTQFTLGILVNCFIELVNGSSWFKTKRMSLSDFIITTL
   hT2R4_    MLRLFYF---------SAIIASVILNFVGIIMNLFITVVNCKTWVKSHRISSSDRILFSL
   mT2R8_    MLWELYV---------FVFAASVFLNFVGIIANLFIIVIIKTWVNSRRIASPDRILFSL
   hT2R5_    MLSAGLG---------LLMLVAVVEFLIGLIGNGSLVVWSFREWIRKFNWSSYNLIILGL 61                                                         120
PTCgene_     SISRLFLHGLLFLSAIQLTHFQKLSEPLNHSYQAIIMLWMIANQANLWLAACLSLLYCSK
   hT2R1_    AVSRIFLQLFIFYVNVI---VIFFIEFIMCS-ANCAILLFIN-ELELWLATWLGVFYCAK
   rT2R1_    ATSRIILQLCILFAQLC---LFSLVRHTLFE-DNITFVFIIN-ELSLWFATWLGVFYCAK
  mT2R19_    ATSRIILQLCILFAQLG---LSCLVRHTLFA-DNVTFVYIIN-ELSLWFATWLGVFYCAK
   hT2R3_    ALLRIILLCIILTDSFLIEFSPNTHDSGIIM-QIIDVSWTFTNHLSIWLATCLGVLYCLK
   hT2R4_    GITRFLMLGLFLVNTIYF-VSSNTERSVYLS-AFFVLCFMFLDSSSVWFVTLLNILYCVK
   mT2R8_    AITRFLTLGLFLLNSVY--IATNTGRSVYFS-TFFLLCWKFLDANSLWLVTILNSLYCVK
   hT2R5_    AGCRFLLQWLIILDLSL---FPLFQSSRWLR--YLSIFWVLVSQASLWFATFLSVFYCKK 121                                                        180
PTCgene_     LIRFSHTFLICLASWVSRKISQMLLGIILCSCICTVLCVWCFFSRPHFTVTTVLFMNNNT
   hT2R1_    VASVRHPLFIWLKMRISKLVPWMILGSLLYVS-MICVFHSKYAGFMVPYFLRKFFSQNAT
   rT2R1_    IATIPHPLFLWLKMRISRLVPWLILGSVLYVI-ITTFIHSRETSAILKPIFISLFPKNAT
  mT2R19_    IATIPHPLFLWLKMRISRLVPWLILASVVYVT-VTTFIHSRETSELPKQIFISFFSKNTT
   hT2R3_    IASFSHPTFLWLKWRVSRVMVWMLLGALLLSCGSTASLINEFKLYSVFRGIEATRNVTEH
   hT2R4_    ITNFQHSVFLLLKRNISPKIPRLLLACVLISA-FTTCLYITLSQASPFPELVTTRNNTSF
   mT2R8_    ITNFQHPVFLLLKRTISMKTTSLLLACLLISA-LTTLLYYMLSQISRFPEHIIGRNDTSF
   hT2R5_    ITTFDRPAYLWLKQRAYNLSLWCLLGYFIINL--LLTVQIGLTFYHPPQGNSSIRYPFES 181                                                        240
PTCgene_     RLNWQIKDLNLFYSFLFCYLWSVPPFLLFLVSSGMLTVSLGRHMRTMKVYTRNSRDPSLE
   hT2R1_    IQKE---DTLAIQIFSF-VAEFSVPLLIFLFAVLLLIFSLGRHTRQMRNTVAGSRVPGRG
   rT2R1_    QVG----TGHATLLSVL-VLGLTLPLFIFTVAVLLLIYSLWNYSRQMR-TMVGTREYSGH
  mT2R19_    RVR----PAHATLLSVF-VFGLTLPFLIFTVAVLLLLSSLWNHSRQMR-TMVGTREPSRH
   hT2R3_    FRKK---RSEYYLIHVLGTLWYLPPLIVSLASYSLLIFSLGRHTRQMLQNGTSSRDPTTE
   hT2R4_    NIS----EGILSLVVSL-VLSSSLQFIINVTSASLLIHSLRRHIQKMQKNATGFWNPQTE
   mT2R8_    DLS----DGILTLVASL-VLNSLLQFMLNVTFASLLIHSLRRHIQKMQRNRTSFWNPQTE
   hT2R5_    WQY-------L-YAFQL-NSGSYLPLVVFLVSSGMLIVSLYTHHKKMKVHSAGRRDVRAK 241                                                        300
PTCgene_     AHIKALKSLVSFFCFFVISSCAAFISVPLLILWRDKIGVMVCVGIMAACPSGHAAILISG
   hT2R1_    APISALLSILSFLILYFSHCMIKVF-LSSLKFHIRRFIFLFFILVIGIYPSGHSLILILG
   rT2R1_    AHISAMLSILSFLILYLSHYMVAVL-ISTQVLYLGSRTFVFCLLVIGMYPSIHSIVLILG
  mT2R19_    ALVSAMLSILSFLILYLSHDMVAVL-ICTQGLHFGSRTFAFCLLVIGMYPSLHSIVLILG
   hT2R3_    AHKRAIRIILSFFFLFLLYFLAFLIASFGNFLPKTKMAKMIGEVMTMFYPAGHSFILILG
   hT2R4_    AHVGAMKLMVYFLILYIPYSVATLVQYLPFYAGMDMGTKSICLIFATLYSPGHSVLIIIT
   mT2R8_    AHMGAMRLMICFLVLYIPYSIATLL-YLPSYMRKNLRAQAICMIITAAYPPGHSVLLIIT
   hT2R5_    AHITALKSLGCFLLHLVYIMASPFSITSKTYPPDLTSVFIWETLMAAYPSLHSLILIMG 301                                               357
PTCgene_     NAKLRRAVMTILLWAQSSLKVRADHKADSRTLC------------------------
   hT2R1_    NPKLKQNAKKFLLHSKCCQ---------------------------------------
   rT2R1_    NPKLKRNAKMFIVHCKCCHCTRAWVTSRSPRLSDLPVPPTHPSANKTSCSEACIMPS
  mT2R19_    NPKLKRNAKTFIVHCKCCHCARAWVTSRNPRLSDLPVPATHHSANKTSCSEACIMPS
   hT2R3_    NSKLKQT---FVVMLR-CESGHLKPGSKGPIFS-------------------------
   hT2R4_    HPKLKTTAKKILCFKK------------------------------------------
   mT2R8_    HHKLKAKAKKIFCFYK------------------------------------------
   hT2R5_    IPRVKQTCQKILWKTVCARRCWGP----------------------------------
```

DNA sequence at nucleotide 145 in the coding region of the PTC gene in families showing linkage to chromosome 7q35-36
g = encodes alanine at amino acid 49, c = encodes proline at amino acid 49

| NO | NAME | PTC | SNP06 17729 | SNP06 17763 | SNP05 26520 | SNP05 28651 | SNP16 34867 | SNP15 41934 | SNP15 41989 | SNP14 42324 | SNP14 42445 | PTC 55283 | PTC 55923 | PTC 56024 | SNP02 71031 | SNP01 72141 | SNP23 112122 | SNP24 121243 |
|---|---|---|---|---|---|---|---|---|---|---|---|---|---|---|---|---|---|---|
| 34 | T.M | 0 | C/C | A/A | G/G | T/T | A/A | C/C | G/G | A/A | T/C | | | | G/C | G/G | C/C | C/C |
| 51 | J.W. | 0 | C/T | G/A | G/A | G/T | A/A | C/C | C/C | A/A | T/T | | | | G/C | G/G | T/T | . |
| 92 | S.Y.L | 0 | C/C | A/A | G/G | G/T | A/A | C/C | C/C | A/A | T/C | | | | G/T | . | C/C | C/C |
| 57 | B.K | 0.1 | C/C | A/A | G/G | T/T | G/A | C/A | G/C | A/A | T/C | | | | G/C | G/G | T/T | T/T |
| 78 | J.C | 0.27 | C/T | G/G | A/A | G/G | A/A | C/A | C/C | A/A | T/C | | | | G/C | g/g | T/C | T/T |
| 16 | Z.A | 0.35 | C/C | G/A | G/A | G/T | A/A | C/A | C/C | A/A | T/T | | | | G/C | G/G | T/C | T/T |
| 61 | D.C | 0.52 | T/T | G/G | A/A | G/G | A/A | C/C | G/G | A/A | T/T | | | | G/C | G/G | T/T | T/T |
| 10 | R.H | 0.57 | C/C | G/A | G/A | G/T | A/A | C/C | C/C | A/A | T/T | | | | . | g/g | T/T | T/T |
| 38 | M.D | 0.57 | C/C | G/A | G/A | G/T | A/A | C/C | C/C | A/A | T/T | | | | G/C | G/G | T/T | T/C |
| 27 | A.D | 0.65 | C/C | A/A | G/A | G/T | A/A | c/a | G/C | A/A | T/T | | | | G/C | G/A | T/C | T/T |
| 94 | H.M | 0.77 | C/C | G/A | G/A | G/T | A/A | C/A | G/G | A/A | T/T | | | | G/C | g/g | T/T | T/T |
| 66 | L.M | 0.92 | C/C | A/A | G/G | T/T | A/A | . | G/G | A/A | T/T | | | | . | . | T/T | T/T |
| 90 | Y.S.L | 0.95 | C/C | A/A | G/G | T/T | A/A | c/a | G/G | A/A | T/T | | | | G/C | g/g | C/C | C/C |
| 82 | E.V.O | 1.4 | C/C | A/A | G/G | T/T | A/A | C/A | G/C | A/A | C/C | | | | G/C | G/G | T/T | T/T |
| 19 | K19-2 | 1.47 | C/C | G/G | A/A | G/G | A/A | C/A | G/C | A/A | T/T | | | | G/C | G/G | T/C | T/T |
| 43 | P.N | 1.65 | C/C | A/A | G/G | T/T | A/A | A/A | C/C | A/A | T/T | | | | G/C | G/G | T/T | T/T |
| 20 | K20-1 | 1.7 | T/T | G/G | A/A | G/G | A/A | C/A | C/C | A/A | C/C | | | | C/C | G/G | C/C | T/T |
| 1 | U.K.K | 1.77 | C/C | A/A | G/A | T/T | A/A | C/C | G/G | A/A | T/T | | | | G/C | G/G | T/T | T/T |
| 87 | Y.G.K | 1.85 | C/C | G/A | G/A | G/T | a/a | C/C | G/G | A/A | T/T | | | | G/C | G/G | T/T | T/T |
| 22 | B.P. | 2.02 | C/T | G/G | A/A | G/G | A/A | C/C | G/G | A/A | T/T | | | | G/C | G/G | C/C | C/C |
| 6 | H.J.P | 2.1 | C/C | G/G | A/A | T/T | A/A | A/A | C/C | A/A | T/T | | | | G/C | G/A | T/T | T/T |
| 19 | K19-1 | 2.35 | C/C | A/A | G/A | T/T | A/A | C/A | C/C | A/A | T/T | C/T | G/C | G/A | G/C | G/A | T/T | t/t |
| 17 | K17-1 | 2.62 | C/C | A/A | G/A | G/G | A/A | C/A | G/G | A/A | T/T | | | | G/C | G/G | T/C | T/C |
| 11 | K11-1 | 2.91 | C/C | A/A | G/A | T/T | G/A | A/A | C/C | A/A | T/T | T/C | G/A | G/G | G/A | T/C | T/C |
| 21 | K21-1 | 3.05 | C/C | G/G | G/A | T/T | G/A | C/A | G/G | A/A | T/C | T/C | G/A | G/G | G/A | T/C | T/C |
| 8 | K8-7 | 3.15 | C/C | A/A | G/A | T/T | A/A | A/A | C/C | A/A | T/T | T/C | G/A | G/G | G/A | C/C | T/C |
| 6 | K6-9 | 3.17 | C/T | G/G | A/A | G/G | A/A | C/A | G/G | A/A | T/T | | | | G/C | G/A | T/T | T/T |
| 74 | C.H | 3.17 | C/C | A/A | G/A | T/T | G/A | C/C | C/C | A/A | T/T | | | | G/C | G/A | T/C | T/C |
| 16 | K16-2 | 3.32 | C/C | G/G | A/A | G/G | A/A | C/A | G/G | A/A | T/T | | | | G/C | G/A | T/C | T/C |
| 72 | M.B | 3.37 | C/C | A/A | G/A | T/T | A/A | C/A | G/G | A/A | T/C | | | | G/G | G/A | T/T | . |
| 40 | M.G | 3.55 | C/C | G/G | A/A | G/G | G/A | C/A | C/C | A/A | T/T | | | | G/C | G/A | T/T | T/T |
| 26 | K26-1 | 3.65 | C/T | G/G | A/A | G/G | G/A | A/A | C/C | A/A | T/C | | | | G/C | G/A | C/C | T/C |
| 27 | K27-1 | 3.7 | C/T | G/G | A/A | G/G | A/A | C/A | C/C | A/A | T/C | | | | G/C | G/A | T/T | T/C |
| 4 | K4-9 | 4.81 | T/T | A/A | G/G | T/T | G/A | A/A | C/C | A/A | T/T | | | | G/C | G/A | C/C | T/T |
| 75 | M.S | 5.15 | C/T | G/G | A/A | G/G | A/A | c/a | C/C | A/A | T/C | | | | G/C | G/A | C/C | C/C |
| 80 | R.A.M | 5.52 | C/T | A/A | A/A | G/G | A/A | C/C | G/G | A/A | T/T | G/C | T/C | G/A | G/G | G/A | C/C | T/C |
| 39 | C.J | 5.77 | T/T | G/G | A/A | G/G | A/A | C/C | G/G | A/A | T/T | | | | G/G | G/A | C/C | T/C |

Figure 7

PHENYLTHIOCARBAMIDE (PTC) TASTE RECEPTOR

CROSS REFERENCE TO RELATED APPLICATIONS

This is a § 371 U.S. National Stage of PCT/US02/23172, filed Jul. 19, 2002 (published in English under PCT Article 21(2)), which in turn claims priority to U.S. Provisional Application No. 60/306,991, filed Jul. 20, 2001. Both applications are incorporated herein in their entirety.

FIELD OF THE INVENTION

The invention provides isolated nucleic and amino acid sequences of a taste cell receptor that serves as a sensor for the bitter taste of phenylthiocarbamide (PTC), antibodies to such PTC taste receptor, methods of detecting such nucleic and amino acid sequences, and methods of screening for modulators of such PTC taste receptor.

BACKGROUND OF THE INVENTION

The ability to taste the bitter compound phenylthiocarbamide (PTC) and related chemicals is bimodal, and all human populations tested to date contain some people who can (tasters) and some people who cannot taste (nontasters) PTC, e.g., the frequency of tasters in North Americans of European ancestry is about 67%. Why this trait has been maintained in the population is uncertain but this polymorphism may have evolved as a key defense mechanism against the ingestion of harmful substances. The gene that gives rise to this phenotype is unknown, and its characterization would permit insights into the mechanism of bitter taste perception and screening for modulators of taste that would be useful in the pharmaceutical, food, and beverage industries to customize taste.

SUMMARY OF THE INVENTION

The present invention relates to the discovery, identification and characterization of nucleotides that encode PTC taste receptor, a receptor protein that serves as a sensor for the bitter taste of phenylthiocarbamide (PTC). The invention encompasses PTC taste receptor nucleotides, host cell expression systems, PTC taste receptor proteins, fusion proteins, polypeptides and peptides, antibodies to the receptor, transgenic animals that express a PTC taste receptor transgene, or recombinant knock-out animals that do not express the PTC taste receptor, antagonists and agonists of the receptor, and other compounds that modulate PTC taste receptor gene expression or PTC taste receptor activity that can be used to block or promote the perception of bitterness.

BRIEF DESCRIPTION OF THE DRAWINGS

FIG. 1 shows human taster PTC taste receptor cDNA sequence (SEQ ID NO: 1) and the deduced amino acid sequence (SEQ ID NO: 2) of human PTC taste receptor.

FIG. 2 shows human nontaster PTC taste receptor cDNA sequence (SEQ ID NO: 3) and the deduced amino acid sequence (SEQ ID NO: 4) of human PTC taste receptor.

FIG. 4 shows sequence alignment of the PTC taste receptor and other mammalian bitter taste receptors, all members of the T2R family as described by Adler et al. 2000 *Cell* 100:693-702. The prefixes on these genes are h—human, r—rat, m—mouse. The alanine mutation in the PTC taste receptor, which causes the nontaster phenotype in humans, is indicated in the sequence at position # 49. PTC gene—SEQ ID NO: 4; hT2R1— SEQ ID NO: 5; rT2R1— SEQ ID NO: 6; mT2R19— SEQ ID NO: 7; hT2R3— SEQ ID NO: 8; hT2R4— SEQ ID NO: 9; mT2R8— SEQ ID NO: 10; hT2R5— SEQ ID NO: 11.

FIG. 7 shows allele sharing in unrelated non-taster individuals. Single nucleotide polymorphisms in clone AC073647.9 typed in a group of 37 unrelated non-taster (PTC taste scores of <6) individuals. The physical locations of the polymorphisms within this clone are indicated in row 2, beginning with SNP06 (2), located at base pair 17,729 within this clone and ending with SNP24, located at base pair 121,243 within this clone. The alleles and the allele frequency for each polymorphism are shown. The boxes marked in dark grey show three SNPs within the candidate gene, located at base pairs 55283, 55923, and 56024, respectively. The boxes marked in light grey show regions of definitive haplotype shared among unrelated non-taster individuals.

DETAILED DESCRIPTION OF THE PREFERRED EMBODIMENT

General

Figure 3:
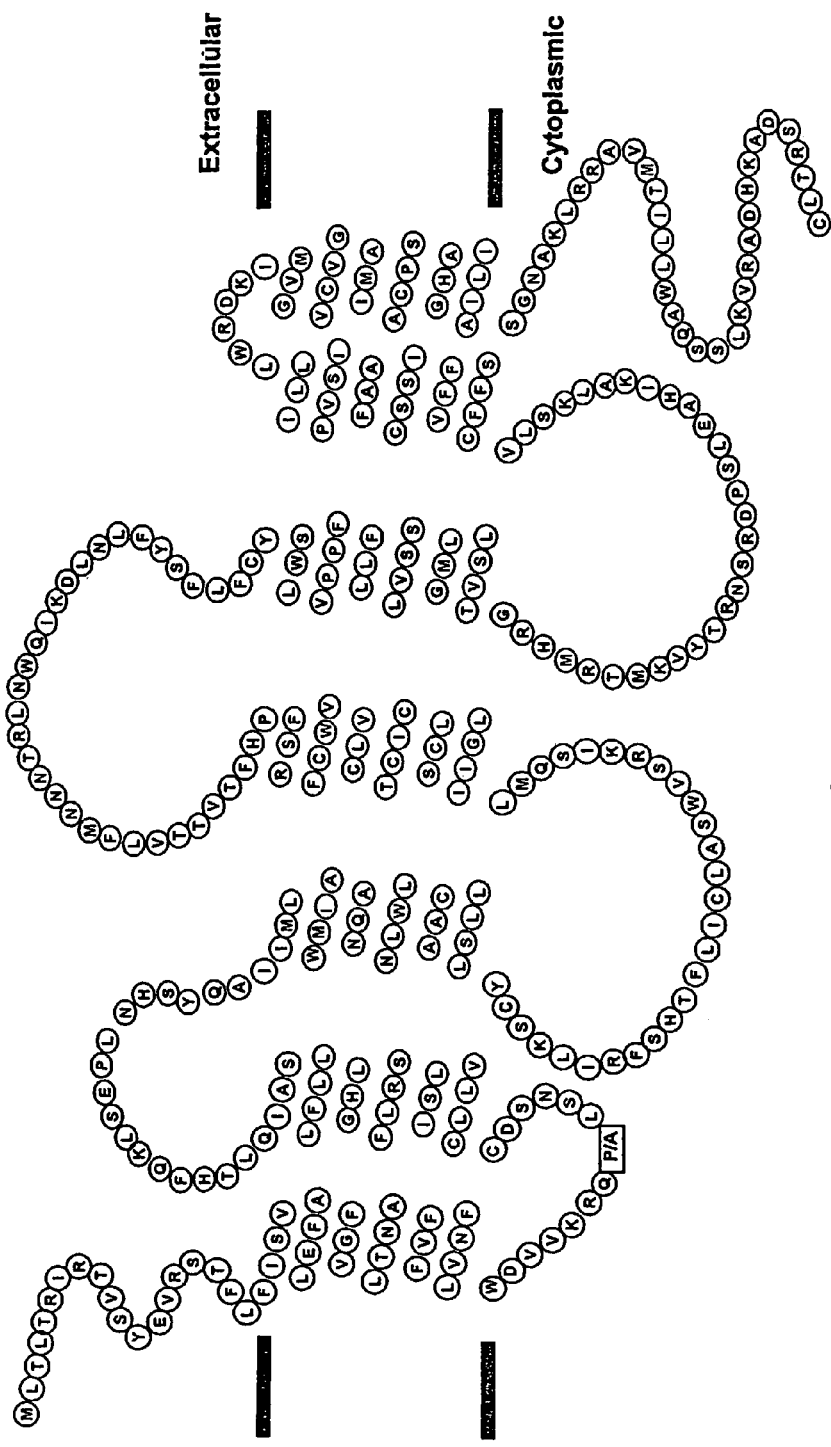
FIG. 3 is a schematic representation of the PTC taste receptor protein showing the seven transmembrane domains, the extracellular and intracellular domains, and the localization of the Ala/Pro mutation at amino acid 49 (SEQ ID NO: 2), which occurs in the first intracellular domain adjacent to the second transmembrane domain.

PTC taste receptor, described for the first time herein, is a novel taste receptor, which serves as a sensor for the bitter taste of phenylthiocarbamide (PTC). PTC taste receptor is a transmembrane G protein-coupled protein that spans the membrane 7 times and belongs to the family of T2R taste receptors. These cell surface receptors interact with tastants and initiate signalling cascades that culminate in neurotransmitter release.

The invention encompasses the use of PTC taste receptor nucleotides, PTC taste receptor proteins and peptides, as well as antibodies to the PTC taste receptor (which can, for example, act as PTC taste receptor agonists or antagonists), antagonists that inhibit receptor activity or expression, or agonists that activate receptor activity or increase its expression.

In particular, the invention described in the sections below encompasses PTC taste receptor, polypeptides or peptides corresponding to functional domains of the PTC taste receptor, e.g., extracellular domains (ECDs), transmembrane domains (TMDs) or cytoplasmic domains (CDs), mutated, truncated or deleted PTC taste receptors (e.g., a PTC taste receptor with one or more functional domains or portions thereof deleted), PTC taste receptor fusion proteins (e.g., a PTC taste receptor or a functional domain of PTC taste receptor, such as an ECD, fused to an unrelated protein or peptide such as an immunoglobulin constant region, i.e., IgFc), nucleotide sequences encoding such products, and host cell expression systems that can produce such PTC taste receptor products.

The invention also encompasses antibodies and anti-idiotypic antibodies (including Fab fragments), antagonists and agonists of the PTC taste receptor, as well as compounds or nucleotide constructs that inhibit expression of the PTC taste receptor gene (transcription factor inhibitors, antisense and ribozyme molecules, or gene or regulatory sequence replacement constructs), or promote expression of PTC taste receptor (e.g., expression constructs in which PTC taste receptor coding sequences are operatively associated with expression control elements such as promoters, promoter/enhancers, etc.). The invention also relates to host cells and animals genetically engineered to express the human PTC taste receptor (or mutants thereof) or to inhibit or "knockout" expression of the animal's endogenous PTC taste receptor.

The PTC taste receptor proteins or peptides, PTC taste receptor fusion proteins, PTC taste receptor nucleotide sequences, host cell expression systems, antibodies, antagonists, agonists and genetically engineered cells and animals can be used for screening for compounds effective in blocking or promoting bitter taste. The use of engineered host cells and/or animals may offer an advantage in that such systems allow not only for the identification of compounds that bind to a ECD of the PTC taste receptor, but can also identify compounds that affect the signal transduced by the activated PTC taste receptor.

Finally, the PTC taste receptor protein products (e.g., soluble derivatives such as peptides corresponding to a PTC taste receptor ECD, or truncated polypeptides lacking a TMD) and fusion protein products (especially PTC taste receptor-Ig fusion proteins, i.e., fusions of the PTC taste receptor or a domain of the PTC taste receptor, e.g., ECD, TMD to an IgFc), antibodies and anti-idiotypic antibodies (including Fab fragments), antagonists or agonists (including compounds that modulate signal transduction which may act on downstream targets in the PTC taste receptor signal transduction pathway) can be used for blocking or promoting bitter taste.

The inhibitors of the invention may be used to enhance the flavor of foods, beverages, and pharmaceuticals by decreasing or eliminating bitter taste features. The inhibitors of the invention could increase food intake in humans or livestock. Moreover, inhibitors of the invention could render pharmaceutical or medical therapies involving bitter compositions more palatable, and improve compliance in drug regimens involving bitter tastants, particularly when administered to children.

The mimics of the invention may be used to worsen the flavor of foods, beverages, and pharmaceuticals by increasing or facilitating bitter taste features. Non-toxic bitter compounds could be used as additives to provoke a desired aversive response, for example, to discourage ingestion of compositions containing these compounds by children, animals, or pests.

The invention is based on the surprising discovery of a new member of the T2R gene family, which is generally known to be involved in bitter taste sensation, and on the equally surprising discovery of a mutation in the gene that correlates with the inability to taste PTC. Resources from so-called CEPH families are administered by the Centre d'Etudes Polymorphisme d'Humain (CEPH, Center for the Study of Human Polymorphisms) in Paris, France. Twenty CEPH families were contacted and evaluated for the ability to taste PTC. Nine of the families had members where some were tasters and others were nontasters. Four of the 9 families show linkage to markers on the long arm of chromosome 7 (7q35-36) in the immediate vicinity of the KEL blood group antigen gene.

Figure 5:
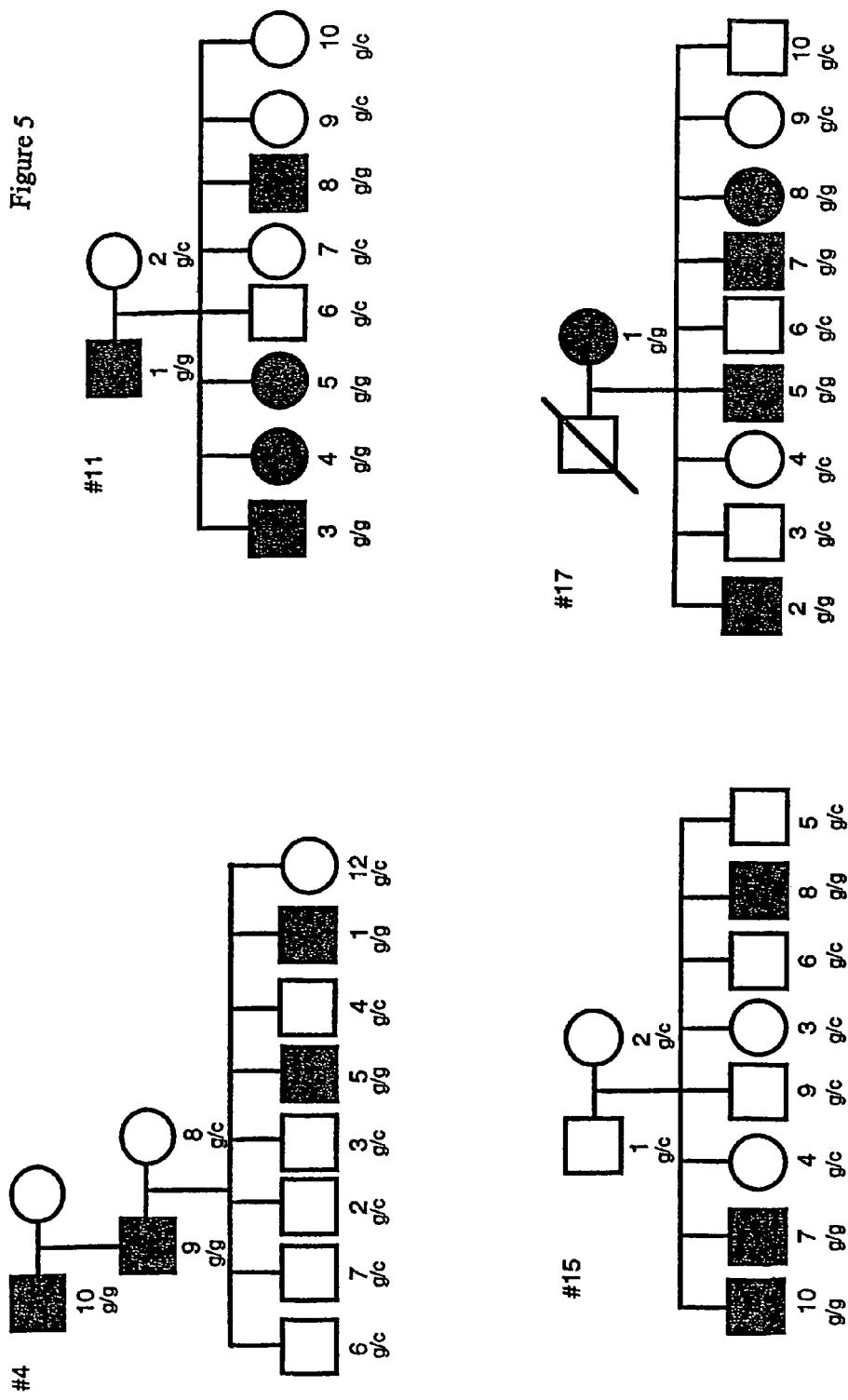
FIG. 5 shows Utah families that show linkage between the inability to taste PTC and markers on chromosome 7. Circles—females, squares—males. Black symbols—PTC nontasters, open symbols—PTC tasters. Mother and Father, on the upper line, give rise to children, shown on the lower line. Beneath each symbol (person) is the amino acid at position 49 in the PTC taste receptor gene that is encoded in their genomic DNA. As expected for a Mendelian trait, everyone who has two copies of the alanine is a nontaster, while everyone with at least one gene encoding the proline is a taster.

High resolution genotyping of the four families displaying linkage to chromosome 7 using additional markers in the KEL region identified markers across a region of approximately 7 Mb of genomic DNA that absolutely co-inherited with PTC taste blindness in these families, and thus defined a critical region in which the PTC nontaster gene resides. The KEL blood antigen gene also lies in this interval of DNA, which resides at 7q35-36. Examination of the emerging DNA sequence of the human genome, Contig GenBank accession no. AC073647.7, clone RP11-707F14, established the presence of a new member of the T2R family, which has not been previously described, and which we designated PTC taste receptor. The PTC taste receptor gene sequence is shown in FIG. 1 (SEQ ID NO: 1). DNA sequencing in this gene identified an apparent mutation in some members of the chromosome 7-linked families shown in FIG. 2 (SEQ ID NO: 3). When present, this mutation causes the amino acid proline at position 49 to be replaced by an alanine (i.e., the nucleotide cytosine "c" at position 145 is replaced by guanine "g"). DNA sequencing in the chromosome 7-linked families showed exact segregation of homozygosity for the alanine form with the inability to taste PTC, following Mendel's laws of inheritance (FIG. 5).

Statistical confidence in the association between the alanine mutation and PTC tasteblindness was quantified using a LOD score. A LOD score of 3, indicating linkage is 1,000-fold more likely than non-linkage, is the standard level for proof in the field. The LOD score for linkage of the alanine mutation to the PTC tasteblindness in these four families is over 7, which corresponds to a likelihood of linkage that is 10,000-fold greater than that typically accepted for demonstration of linkage.

Referring to FIGS. 3 and 4, the PTC taste receptor, like other members of the T2R bitter taste receptor family, is a G protein-coupled receptor characterized by 7 transmembrane domains. In contrast to T1R5, which belong to the superfamily of G protein-coupled receptors having a large N-terminal domain, the PTC taste receptor has only a short extracellular N terminus. While individual members of the T2R family exhibit 30%-70% amino acid identity, the amino acid identity between the PTC taste receptor and the other T2R proteins is less than 30%. The most highly conserved sequence motifs reside in the first and last transmembrane segments, and also in the second cytoplasmic loop. The most divergent regions are the extracellular segments, extending partway into the transmembrane helices, presumably reflecting the need to recognize many structurally diverse ligands.

The crucial alanine occurs in the first intracellular domain at amino acid 49, and is adjacent to the second transmembrane domain.

Various aspects of the invention are described in greater detail in the sections below.

Definitions

The term "isolated" requires that a material be removed from its original environment (e.g., the natural environment if it is naturally occurring). For example, a naturally occurring polynucleotide or polypeptide present in a living cell is not isolated, but the same polynucleotide or polypeptide, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

The PTC Taste Receptor Gene

The cDNA sequence (SEQ ID NO: 1) and deduced amino acid sequence (SEQ ID NO: 2) of the PTC taste receptor (of tasters) are shown in FIG. 1. The cDNA sequence (SEQ ID NO: 3) and deduced amino acid sequence (SEQ ID NO: 4) of the PTC taste receptor (of nontasters) are shown in FIG. 2. The "wild-type" form contains the amino acid proline at amino acid position 49, while the "mutant" form contains an alanine at this position (i.e., the wild-type form contains the nucleotide "c" at position 145, while the mutant form contains "g" at this position). Tasteblindness is an autosomal recessive trait caused by a proline to alanine mutation at position 49 of the PTC taste receptor on both of the individual's chromosomes.

The PTC taste receptor nucleotide sequences of the invention include: (a) the DNA sequences shown in FIGS. 1 (SEQ ID NO: 1) and 2 (SEQ ID NO: 3); (b) nucleotide sequences that encode the amino acid sequences shown in FIG. 1 (SEQ ID NO: 2) and 2 (SEQ ID NO: 4); (c) any nucleotide sequence that hybridizes to the complement of the DNA sequences that encode the amino acid sequence shown in FIG. 1 (SEQ ID NO: 2) and 2 (SEQ ID NO: 4) under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al. eds. 1989 *Current Protocols in Molecular Biology* Vol. I, Green Publishing Associates, Inc., and John Wiley & sons, Inc., New York, at p. 2.10.3) and encodes a functionally equivalent gene product; and (d) any nucleotide sequence that hybridizes to the complement of the DNA sequences that encode the amino acid sequence shown in FIG. 1 (SEQ ID NO: 2) and 2 (SEQ ID NO: 4) under less stringent conditions, such as moderately stringent conditions, e.g., washing in 0.2×SSC/0.1% SDS at 42° C. (Ausubel et al. eds. 1989 *Current Protocols in Molecular Biology* Vol. I, Green Publishing Associates, Inc., and John Wiley & sons, Inc., New York, at p. 2.10.3), yet which still encodes a functionally equivalent PTC taste receptor gene product. Functional equivalents of the PTC taste receptor include naturally occurring PTC taste receptor present in other species, and mutant PTC taste receptors whether naturally occurring or engineered. The invention also includes degenerate variants of sequences (a) through (d).

The invention also includes nucleic acid molecules, preferably DNA molecules that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as PTC taste receptor antisense molecules, useful, for example, in PTC taste receptor gene regulation (and/or as antisense primers in amplification reactions of PTC taste receptor gene nucleic acid sequences). Further, such sequences may be used as part of ribozyme and/or triple helix sequences, also useful for PTC taste receptor gene regulation. Still further, such molecules may be used as components of diagnostic methods whereby, for example, the presence of the "wild-type" or "mutant" PTC taste receptor allele responsible for causing the taster or nontaster phenotype may be detected.

In addition to the PTC taste receptor nucleotide sequences described above, full length PTC taste receptor cDNA or gene sequences present in the same species and/or homologs of the PTC taste receptor gene present in other species can be identified and readily isolated, without undue experimentation, by molecular biological techniques well known in the art. The identification of homologs of PTC taste receptor in related species can be useful for developing animal model systems more closely related to humans for purposes of drug discovery. For example, expression libraries of cDNAs synthesized from lingual epithelium mRNA derived from the organism of interest can be screened using labeled PTC. Alternatively, such cDNA libraries, or genomic DNA libraries derived from the organism of interest can be screened by hybridization using the nucleotides described herein as hybridization or amplification probes. Using a computer program such as BLAST or BLASTN, electronic sequence database search tools can be employed where the programs provide a "default" opening penalty and a "default" gap penalty, and a scoring matrix such as PAM 250 (a standard scoring matrix, see Dayhoff et al. in: *Atlas of Protein Sequence and Structure*, vol. 5, sup. 3, 1978). Furthermore, genes at other genetic loci within the genome that encode proteins which have extensive homology to one or more domains of the PTC taste receptor gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15-30 base pairs of the PTC taste receptor nucleotide sequence, as shown in FIG. 1 (SEQ ID NO: 1) and 2 (SEQ ID NO: 3). The hybridization washing conditions used should be of a lower stringency when the cDNA library is derived from an organism different from the type of organism from which the labeled sequence was derived. With respect to the cloning of a mouse PTC taste receptor homolog, using human PTC taste receptor probes, for example, hybridization can, for example, be performed at 65° C. overnight in Church's buffer (7% SDS, 250 mM NaHPO$_4$, 2 μM EDTA, 1% BSA). Washes can be done with 2×SSC, 0.1% SDS at 65° C. and then at 0.1×SSC, 0.1% SDS at 65° C.

Low stringency conditions are well known to those of skill in the art, and will vary predictably depending on the specific organisms from which the library and the labeled sequences are derived. For guidance regarding such conditions see, for example, Sambrook et al. 1989 *Molecular Cloning, A Laboratory Manual*, Cold Springs Harbor Press, N.Y.; and Ausubel et al. 1989 *Current Protocols in Molecular Biology* Green Publishing Associates and Wiley Interscience, N.Y.

Alternatively, the labeled PTC taste receptor nucleotide probe may be used to screen a genomic library derived from the organism of interest, again, using appropriately stringent conditions. The identification and characterization of human genomic clones is helpful for designing drug screening protocols for identifying bitter taste blockers or mimics. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics, although the PTC taste receptor described herein does not contain introns that interrupt coding regions.

Further, a PTC taste receptor gene homolog may be isolated from nucleic acid of the organism of interest by performing PCR using two degenerate oligonucleotide primer pools designed on the basis of amino acid sequences within the PTC taste receptor gene product disclosed herein. The template for the reaction may be cDNA obtained by reverse transcription of mRNA prepared from, for example, human or non-human cell lines or tissue, such as lingual epithelium, known or suspected to express a PTC taste receptor gene allele.

The PCR product may be subcloned and sequenced to ensure that the amplified sequences represent the sequences of a PTC taste receptor gene. The PCR fragment may then be used to isolate a full-length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full-length cDNA sequences. For example, RNA may be isolated, following standard procedures, from an appropriate cellular or tissue source (i.e., one known, or suspected, to express the PTC taste receptor gene, such as, for example, lingual epithelium). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies, which may be used, see, e.g., Sambrook et al. 1989 *Molecular Cloning, A Laboratory Manual*, Cold Springs Harbor Press, N.Y.

The PTC taste receptor gene sequences may additionally be used to isolate mutant PTC taste receptor gene alleles. Such mutant alleles may be isolated from individuals known or proposed to have a genotype that contributes to the symptoms of bitter tasteblindness. Mutant alleles and mutant allele products may then be utilized in the screening systems described below. Additionally, such PTC taste receptor gene sequences can be used to detect PTC taste receptor gene regulatory (e.g., promoter or promoter/enhancer) effects, which can affect sensitivity to bitter taste.

A cDNA of a mutant PTC taste receptor gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant PTC taste receptor allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant PTC taste receptor allele to that of the normal PTC taste receptor allele, the mutation(s) responsible for the loss or alteration of function of the mutant PTC taste receptor gene product can be ascertained.

Alternatively, a genomic library can be constructed using DNA obtained from an individual suspected of or known to carry the mutant PTC taste receptor allele, or a cDNA library can be constructed using RNA from a tissue known, or suspected, to express the mutant PTC taste receptor allele. The normal PTC taste receptor gene or any suitable fragment thereof may then be labeled and used as a probe to identify the corresponding mutant PTC taste receptor allele in such libraries. Clones containing the mutant PTC taste receptor gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant PTC taste receptor allele in an individual suspected of or known to carry such a mutant allele. In this manner, gene products made by the putatively mutant tissue may be expressed and screened using standard antibody screening techniques in conjunction with antibodies raised against the normal PTC taste receptor gene product as described in the sections below. (For screening techniques, see, for example, Harlow, E. and Lane, eds. 1988 *Antibodies: A Laboratory Manual*, Cold Spring Harbor Press, Cold Spring Harbor). In cases where a PTC taste receptor mutation results in an expressed gene product with altered function (e.g., as a result of a missense or a frameshift mutation), a polyclonal set of antibodies to PTC taste receptor are likely to cross-react with the mutant PTC taste receptor gene product. Library clones detected via their reaction with such labeled antibodies can be purified and subjected to sequence analysis according to methods well known to those of skill in the art.

The invention also encompasses nucleotide sequences that encode mutant PTC taste receptors, peptide fragments of the PTC taste receptor, truncated PTC taste receptors, and PTC taste receptor fusion proteins. These include, but are not limited to nucleotide sequences encoding mutant PTC taste receptors described in the sections below; polypeptides or peptides corresponding to ECD, TMD and/or CD of the PTC taste receptor or portions of these domains; truncated PTC taste receptor in which one or two of the domains is deleted, e.g., a soluble PTC taste receptor lacking TMDs or both the TMD and CD regions, or a truncated, nonfunctional PTC taste receptor lacking all or a portion of CD regions. Nucleotides encoding fusion proteins may include but are not limited to full length PTC taste receptor, truncated PTC taste receptor or peptide fragments of PTC taste receptor fused to an unrelated protein or peptide, such as for example, a transmembrane sequence, which anchors the PTC taste receptor ECD to the cell membrane; an IgFc domain which increases the stability and half life of the resulting fusion protein (e.g., PTC taste receptor-Ig) in the bloodstream; or an enzyme, fluorescent protein, luminescent protein which can be used as a marker.

The invention also encompasses (a) DNA vectors that contain any of the foregoing PTC taste receptor coding sequences and/or their complements (i.e., antisense); (b) DNA expression vectors that contain any of the foregoing PTC taste receptor coding sequences operatively associated with a regulatory element that directs the expression of the coding sequences; and (c) genetically engineered host cells that contain any of the foregoing PTC taste receptor coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

PTC Taste Receptor Proteins and Polypeptides

PTC taste receptor protein, polypeptides and peptide fragments, mutated, truncated or deleted forms of the PTC taste receptor and/or PTC taste receptor fusion proteins can be prepared for a variety of uses, including but not limited to the generation of antibodies, as reagents in diagnostic assays, the identification of other cellular gene products involved in the regulation of bitter sensitivity, as reagents in assays for screening for compounds that can be used as bitter taste blockers or mimics, and as pharmaceutical reagents useful in blocking or mimicking bitter tastes related to the PTC taste receptor.

The PTC taste receptor amino acid sequences of the invention include the amino acid sequences shown in FIGS. 1 (SEQ ID NO: 2) and 2 (SEQ ID NO: 4). Further, PTC taste receptors of other species are encompassed by the invention. In fact, any PTC taste receptor proteins encoded by the PTC taste receptor nucleotide sequences described in the section above are within the scope of the invention.

The invention also encompasses proteins that are functionally equivalent to the PTC taste receptor encoded by the nucleotide sequences described herein, as judged by the ability to bind PTC, the binding affinity for PTC, the resulting biological effect of PTC binding, e.g., signal transduction, a change in cellular metabolism (e.g., ion flux, phosphorylation) or change in phenotype when the PTC taste receptor equivalent is present in an appropriate cell type (such as ability or inability to taste PTC or related compounds). Such functionally equivalent PTC taste receptor proteins include but are not limited to additions or substitutions of amino acid residues within the amino acid sequence encoded by the PTC taste receptor nucleotide sequences described herein, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. While random mutations can be made to PTC taste receptor DNA (using random mutagenesis techniques well known to those skilled in the art) and the resulting mutant PTC taste receptors tested for activity, site-directed mutations of the PTC taste receptor coding sequence can be engineered (using site-directed mutagenesis techniques well known to those skilled in the art) to generate mutant PTC taste receptors with decreased function, e.g., lower binding affinity for PTC, and/or decreased signal transduction capacity (or with increased function, e.g., higher binding affinity for PTC, and/or increased signal transduction capacity).

For example, the alignment of several T2R receptors and the human PTC taste receptor is shown in FIG. 4. Mutant PTC taste receptors can be engineered so that regions of identity are maintained, whereas the variable residues are altered, e.g., by deletion or insertion of an amino acid residue(s) or by substitution of one or more different amino acid residues. Conservative alterations at the variable positions can be engineered in order to produce a mutant PTC taste receptor that retains function; e.g., PTC binding affinity or signal transduction capability or both. Non-conservative changes can be engineered at these variable positions to alter function, e.g., PTC binding affinity or signal transduction capability, or both. Alternatively, where alteration of function is desired, deletion or non-conservative alterations of the conserved regions can be engineered. For example, deletion or non-conservative alterations (substitutions or insertions) of a CD of human PTC taste receptor, or portions of a CD, can be engineered to produce a mutant PTC taste receptor that binds PTC but is signalling-incompetent. Non-conservative alterations in the regions of identity can be engineered to produce mutant PTC taste receptors with altered binding affinity for PTC.

Other mutations to the PTC taste receptor coding sequence can be made to generate PTC taste receptors that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the ECD (N-X-S or N-X-T), and/or an amino acid deletion at the second position of any one or more such recognition sequences in the ECD will prevent glycosylation of the PTC taste receptor at the modified tripeptide sequence. (See, e.g., Miyajima et al. 1986 *EMBO J.* 5:1193-1197).

Peptides corresponding to one or more domains of the PTC taste receptor (e.g., an ECD, a TMD or a CD), truncated or deleted PTC taste receptors (e.g., PTC taste receptor in which a TMD and/or a CD is deleted) as well as fusion proteins in which the full length PTC taste receptor, a PTC taste receptor peptide, or truncated PTC taste receptor is fused to another protein are also within the scope of the invention and can be designed on the basis of the PTC taste receptor nucleotide and PTC taste receptor amino acid sequences disclosed herein. Such fusion proteins include but are not limited to IgFc fusions which stabilize the PTC taste receptor protein or peptide and prolong half-life in vivo; or fusions to any amino acid sequence that allows the fusion protein to be targeted and/or anchored to the cell membrane (e.g., first 20 amino acids of rhodopsin), allowing an ECD to be exhibited on the cell surface; or fusions to an enzyme, fluorescent protein, or luminescent protein which provide a marker function.

While the PTC taste receptor polypeptides and peptides can be chemically synthesized (e.g., see Creighton 1983 *Proteins: Structures and Molecular Principles* W. H. Freeman & Co., N.Y.), large polypeptides derived from the PTC taste receptor and the full length PTC taste receptor itself may advantageously be produced by recombinant DNA technology using techniques well known in the art for expressing nucleic acid containing PTC taste receptor gene sequences and/or coding sequences. Such methods can be used to construct expression vectors containing the PTC taste receptor nucleotide sequences described herein and appropriate transcriptional and translational control signals. These methods include, for example, in vitro recombinant DNA techniques, synthetic techniques, and in vivo genetic recombination. See, for example, the techniques described in Sambrook et al. 1989 *Molecular Cloning, A Laboratory Manual*, Cold Springs Harbor Press, N.Y., and Ausubel et al. 1989 *Current Protocols in Molecular Biology* Green Publishing Associates and Wiley Interscience, N.Y. Alternatively, RNA capable of encoding PTC taste receptor nucleotide sequences may be chemically synthesized using, for example, automated nucleic acid synthesizers. See, for example, the techniques described in Gait, M. J. ed. 1984 *Oligonucleotide Synthesis* IRL Press, Oxford.

A variety of host-expression vector systems may be utilized to express the PTC taste receptor nucleotide sequences of the invention. Where the PTC taste receptor peptide or polypeptide is a soluble derivative (e.g., PTC taste receptor peptides corresponding to an ECD; truncated or deleted PTC taste receptor in which TMD and/or CD are deleted) the peptide or polypeptide can be recovered from the culture, i.e., from the host cell in cases where the PTC taste receptor peptide or polypeptide is not secreted, and from the culture media in cases where the PTC taste receptor peptide or polypeptide is secreted by the cells. However, the expression systems also encompass engineered host cells that express the PTC taste receptor or functional equivalents in situ, i.e., anchored in the cell membrane. Purification or enrichment of the PTC taste receptor from such expression systems can be accomplished using appropriate detergents and lipid micelles and methods well known to those skilled in the art. However, such engineered host cells themselves may be used in situations where it is important not only to retain the structural and functional characteristics of the PTC taste receptor, but also to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing PTC taste receptor nucleotide sequences; yeast (e.g., *Saccharomyces, Pichia*) transformed with recombinant yeast expression vectors containing the PTC taste receptor nucleotide sequences; insect cell systems (e.g., *Spodoptera frugiperda, Autographa californica*) infected with recombinant virus expression vectors (e.g., baculovirus) containing the PTC taste receptor sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing PTC taste receptor nucleotide sequences; or mammalian cell systems (e.g., COS, CHO, BHK, HEK293, 3T3) harboring recombinant expression constructs containing promoters derived from the genome of mammalian cells (e.g., metallothionein promoter, EFI alpha promoter) or from mammalian viruses (e.g., the adenovirus late promoter; the vaccinia virus 7.5K promoter).

In bacterial systems, a number of expression vectors may be advantageously selected depending upon the use intended for the PTC taste receptor gene product being expressed. For example, when a large quantity of such a protein is to be produced, vectors, which direct the expression of high levels of fusion protein products that are readily purified, may be desirable. Such vectors include, but are not limited to the *E. coli* expression vector pUR278 (Ruther et al. 1983 *EMBO J.* 2:1791), in which the PTC taste receptor coding sequence may be ligated individually into the vector in frame with the lacZ coding region so that a fusion protein is produced; pIN vectors (Inouye & Inouye 1985 *Nucleic Acids Res* 13:3101-3109; Van Heeke & Schuster 1989 *J Biol Chem* 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The PTC taste receptor gene coding sequence may be cloned individually into non-essential regions (for example the polyhedrin gene) of the virus and placed under control of an AcNPV promoter (for example the polyhedrin promoter). Successful insertion of PTC taste receptor gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al. 1983 *J Virol* 46:584; Smith, U.S. Pat. No. 4,215,051).

In mammalian host cells, a number of viral-based expression systems may be utilized. In cases where an adenovirus is used as an expression vector, the PTC taste receptor nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the PTC taste receptor gene product in infected hosts. For example, see Logan & Shenk 1984 *PNAS USA* 81:3655-3659. Specific initiation signals may also be required for efficient translation of inserted PTC taste receptor nucleotide sequences. These signals include the ATG initiation codon and adjacent sequences. In cases where an entire PTC taste receptor gene or cDNA, including its own initiation codon and adjacent sequences, is inserted into the appropriate expression vector, no additional translational control signals may be needed. However, in cases where only a portion of the PTC taste receptor coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See, Bittner et al. 1987 *Methods in Enzymol* 153:516-544).

In addition, a host cell strain may be chosen, which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, HEK293, 3T3 and WI38.

For long-term, high-yield production of recombinant proteins, stable expression is preferred. For example, cell lines that stably express the PTC taste receptor sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the PTC taste receptor gene product. Such engineered cell lines may be particularly useful in screening and evaluation of compounds that affect the endogenous activity of the PTC taste receptor gene product.

A number of selection systems may be used, including but not limited to the herpes simplex virus thymidine kinase (Wigler et al. 1977 *Cell* 11:223), hypoxanthine-guanine phosphoribosyltransferase (Szybalska & Szybalski 1962 *PNAS USA* 48:2026), and adenine phosphoribosyltransferase (Lowy et al. 1980 *Cell* 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al. 1980 *PNAS USA* 77:3567; O'Hare, et al. 1981 PNAS USA 78:1527); gpt, which confers resistance to mycophenolic acid (Mulligan & Berg 1981 *PNAS USA* 78:2072); neo, which confers resistance to the aminoglycoside G-418 (Colberre-Garapin et al. 1981 *J Mol Biol* 150:1); and hygro, which confers resistance to hygromycin (Santerre et al. 1984 *Gene* 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al. 1991 *PNAS USA* 88:8972-8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

The PTC taste receptor gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate PTC taste receptor transgenic animals.

Any technique known in the art may be used to introduce the PTC taste receptor transgene into animals to produce the founder lines of transgenic animals. Such techniques include, but are not limited to pronuclear microinjection (Hoppe, P. C. and Wagner, T. E. 1989 U.S. Pat. No. 4,873, 191); retrovirus mediated gene transfer into germ lines (Van der Putten et al. 1985 *PNAS USA* 82:6148-6152); gene targeting in embryonic stem cells (Thompson et al. 1989 *Cell* 56:313-321); electroporation of embryos (Lo 1983 *Mol Cell Biol* 3:1803-1814); and sperm-mediated gene transfer (Lavitrano et al. 1989 *Cell* 57:717-723); etc. For a review of such techniques, see Gordon 1989 *Intl Rev Cytol* 115:171-229.

The present invention provides for transgenic animals that carry the PTC taste receptor transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al. 1992 *PNAS USA* 89:6232-6236). The regulatory sequences required for such a cell-type specific activation will depend upon the particular cell type of interest, and will be apparent to those of skill in the art. When it is desired that the PTC taste receptor gene transgene be integrated into the chromosomal site of the endogenous PTC taste receptor gene, gene targeting is preferred. Briefly, when such a technique is to be utilized, vectors containing some nucleotide sequences homologous to the endogenous PTC taste receptor gene are designed for the purpose of integrating, via homologous recombination with chromosomal sequences, into and disrupting the function of the nucleotide sequence of the endogenous PTC taste receptor gene. The transgene may also be selectively introduced into a particular cell type, thus inactivating the endogenous PTC taste receptor gene in only that cell type, by following, for example, the teaching of Gu et al. (Gu, et al. 1994 *Science* 265:103-106). The regulatory sequences required for such a cell-type specific inactivation will depend upon the particular cell type of interest, and will be apparent to those of skill in the art.

Once transgenic animals have been generated, the expression of the recombinant PTC taste receptor gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of PTC taste receptor gene-expressing tissue, may also be evaluated immunocytochemically using antibodies specific for the PTC taste receptor transgene product.

Antibodies to PTC Taste Receptor Proteins

Antibodies that specifically recognize one or more epitopes of PTC taste receptor, or epitopes of conserved variants of PTC taste receptor, or peptide fragments of the PTC taste receptor are also encompassed by the invention. Such antibodies include but are not limited to polyclonal antibodies, monoclonal antibodies (mAbs), humanized or chimeric antibodies, single chain antibodies, Fab fragments, F (ab')₂ fragments, fragments produced by a Fab expression library, anti-idiotypic (anti-Id) antibodies, and epitope-binding fragments of any of the above.

The antibodies of the invention may be used, for example, in the detection of the "wild-type" or "mutant" PTC taste receptor in a biological sample and may, therefore, be utilized as part of a diagnostic technique whereby individuals may be tested for being tasters or nontasters. The antibodies of the invention may be utilized in conjunction with, for example, compound screening schemes, as described in the sections below, for the evaluation of the effect of test compounds on expression and/or activity of the PTC taste receptor gene product. Such antibodies may additionally be used as a method for the inhibition of bitter taste.

For the production of antibodies, various host animals may be immunized by injection with the PTC taste receptor, a PTC taste receptor peptide (e.g., one corresponding the a functional domain of the receptor, such as an ECD, a TMD, or a CD), truncated PTC taste receptor polypeptides (PTC taste receptor in which one or more domains, e.g., a TMD or a CD, has been deleted), functional equivalents of the PTC taste receptor or mutants of the PTC taste receptor. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975 *Nature* 256:495-497; and U.S. Pat. No. 4,376,110), the human B-cell hybridoma technique (Kosbor et al. 1983 *Immunology Today* 4:72; Cole et al. 1983 *PNAS USA* 80:2026-2030), and the EBV-hybridoma technique (Cole et al. 1985 *Monoclonal Antibodies And Cancer Therapy*, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al. 1984 *PNAS USA* 81:6851-6855; Neuberger et al. 1984 *Nature* 312:604-608; Takeda et al. 1985 *Nature* 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird 1988 *Science* 242:423-426; Huston et al. 1988 *PNAS USA* 85:5879-5883; and Ward et al. 1989 *Nature* 334:544-546) can be adapted to produce single chain antibodies against PTC taste receptor gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. 1989 *Science* 246:1275-1281) to allow rapid and easy identification of monoclonal Fab fragments with the desired specificity.

Antibodies to the PTC taste receptor can, in turn, be utilized to generate anti-idiotype antibodies that "mimic" the PTC taste receptor, using techniques well known to those skilled in the art. (See, e.g., Greenspan & Bona 1993 *FASEB J* 7:437-444; and Nissinoff 1991 *J Immunol* 147:2429-2438). For example antibodies which bind to the PTC taste receptor ECD and competitively inhibit the binding of PTC to the PTC taste receptor can be used to generate anti-idiotypes that "mimic" the ECD and, therefore, bind and neutralize PTC. Such neutralizing anti-idiotypes or Fab fragments of such anti-idiotypes can be used in pharmaceuticals to neutralize PTC and promote sweetness.

Screening Assays for Compounds that Modulate PTC Taste Receptor Expression or Activity The following assays are designed to identify compounds that interact with (e.g., bind to) PTC taste receptor (including, but not limited to an ECD or a CD or a TMD of PTC taste receptor), compounds that interact with (e.g., bind to) intracellular proteins that interact with PTC taste receptor (including, but not limited to, a TMD or a CD of PTC taste receptor), compounds that interfere with the interaction of PTC taste receptor with transmembrane or intracellular proteins involved in PTC taste receptor-mediated signal transduction, and to compounds which modulate the activity of PTC taste receptor gene (i.e., modulate the level of PTC taste receptor gene expression) or modulate the level of PTC taste receptor activity. Assays may additionally be utilized which identify compounds which bind to PTC taste receptor gene regulatory sequences (e.g., promoter sequences) and which may modulate PTC taste receptor gene expression. See, e.g., Platt, K. A. 1994 *J Biol Chem* 269:28558-28562.

The compounds which may be screened in accordance with the invention include, but are not limited to peptides, antibodies and fragments thereof, and other organic compounds (e.g., peptidomimetics, small molecules) that bind to one or more ECDs of the PTC taste receptor and either mimic the activity triggered by the natural ligand (i.e., agonists) or inhibit the activity triggered by the natural ligand (i.e., antagonists); as well as peptides, antibodies or fragments thereof, and other organic compounds that mimic the ECD of the PTC taste receptor (or a portion thereof) and bind to and "neutralize" natural ligand.

Such compounds may include, but are not limited to, peptides such as, for example, soluble peptides, including but not limited to members of random peptide libraries; (see, e.g., Lam, K. S. et al. 1991 *Nature* 354:82-84; Houghten, R. et al. 1991 *Nature* 354:84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al. 1993 *Cell* 72:767-778), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds which can be screened in accordance with the invention include but are not limited to small organic molecules that are able to gain entry into an appropriate cell and affect the expression of the PTC taste receptor gene or some other gene involved in the PTC taste receptor signal transduction pathway (e.g., by interacting with the regulatory region or transcription factors involved in gene expression); or such compounds that affect the activity of the PTC taste receptor or the activity of some other intracellular factor involved in the PTC taste receptor signal transduction pathway.

Computer modeling and searching technologies permit identification of compounds, or the improvement of already identified compounds, that can modulate PTC taste receptor expression or activity. Having identified such a compound or composition, the active sites or regions are identified. Such active sites might typically be ligand binding sites, such as the interaction domains of PTC with PTC taste receptor itself, or the interaction domains of PTC with the "wild-type" PTC taste receptor in comparison to the interaction domains of PTC with the "mutant" PTC taste receptor (to reproduce the effect of the alanine substitution for designing bitter taste blockers, or to reproduce the effect of the proline substitution for designing bitter taste mimics). The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures, such as high resolution electron microscopy. The geometric structures may be measured with a complexed ligand, natural or artificial, which may increase the accuracy of the active site structure determined. In another embodiment, the structure of the "wild-type" taste receptor is compared to that of the "mutant" taste receptor and, rather than solve the entire structure, the structure is solved for the protein domains that are changed.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential PTC taste receptor modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

In another embodiment, the structure of the "wild-type" taste receptor is compared to that of the "mutant" taste receptor. Then, potential bitter taste inhibitors are designed that bring about a structural change in the "wild-type" form so that it resembles the "mutant" form. Or, potential bitter taste mimics are designed that bring about a structural change in the "mutant" form so that it resembles the "wild-type" form.

Further experimental and computer modeling methods useful to identify modulating compounds based upon identification of the active sites of PTC, "wild-type" and "mutant" PTC taste receptor, and related transduction and transcription factors will be apparent to those of skill in the art.

Examples of molecular modeling systems are the CHARMM and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al. 1988 *Acta Pharmaceutical Fennica* 97:159-166; Ripka 1988 *New Scientist* 54-57; McKinaly and Rossmann 1989 *Annu Rev Pharmacol Toxicol* 29:111-122; Perry and Davies 1989 OSAR: *Quantitative Structure-Activity Relationships in Drug Design pp.* 189-193 (Alan R. Liss, Inc.); Lewis and Dean 1989 *Proc R Soc Lond* 236:125-140 and 141-162; and, with respect to a model receptor for nucleic acid components, Askew, et al. 1989 *J Am Chem Soc* 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the PTC taste receptor gene product, and for designing bitter taste blockers and mimics.

In Vitro Screening Assays for Compounds that Bind to PTC Taste Receptor.

In vitro systems may be designed to identify compounds capable of interacting with (e.g., binding to) PTC taste receptor (including, but not limited to, an ECD, or a TMD, or a CD of PTC taste receptor). Compounds identified may be useful, for example, in modulating the activity of "wild type" and/or "mutant" PTC taste receptor gene products; may be useful in elaborating the biological function of the PTC taste receptor; may be utilized in screens for identifying compounds that disrupt normal PTC taste receptor interactions; or may in themselves disrupt such interactions.

The principle of the assays used to identify compounds that bind to the PTC taste receptor involves preparing a reaction mixture of the PTC taste receptor polypeptide and a test compound under conditions and for a time sufficient to allow the two components to interact and bind, thus forming a complex which can be removed and/or detected in the reaction mixture. The PTC taste receptor species used can vary depending upon the goal of the screening assay. For example, where agonists or antagonists of the PTC are sought, the full length PTC taste receptor, or a soluble truncated PTC taste receptor, e.g., in which a TMD and/or a CD is deleted from the molecule, a peptide corresponding to an ECD or a fusion protein containing a PTC taste receptor ECD fused to a protein or polypeptide that affords advantages in the assay system (e.g., labeling, isolation of the resulting complex, etc.) can be utilized. Where compounds that interact with the cytoplasmic domain are sought to be identified, peptides corresponding to a PTC taste receptor CD and fusion proteins containing a PTC taste receptor CD can be used.

The screening assays can be conducted in a variety of ways. For example, one method to conduct such an assay would involve anchoring the PTC taste receptor protein, polypeptide, peptide or fusion protein or the test substance onto a solid phase and detecting PTC taste receptor/test compound complexes anchored on the solid phase at the end of the reaction. In one embodiment of such a method, the PTC taste receptor reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for PTC taste receptor protein, polypeptide, peptide or fusion protein or the test compound to anchor any complexes formed in solution, and a labeled antibody specific for the other component of the possible complex to detect anchored complexes.

Alternatively, cell-based assays, membrane vesicle-based assays and membrane fraction-based assays can be used to identify compounds that interact with PTC taste receptor. To this end, cell lines that express PTC taste receptor, or cell lines (e.g., COS cells, CHO cells, HEK293 cells, etc.) have been genetically engineered to express PTC taste receptor (e.g., by transfection or transduction of PTC taste receptor DNA) can be used. Interaction of the test compound with, for example, an ECD or a CD of PTC taste receptor expressed by the host cell can be determined by comparison or competition with PTC.

A PTC taste receptor polypeptide (receptor of the present invention) may be employed in a screening process for compounds which bind the receptor and which activate (agonists) or inhibit activation (antagonists) of the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al. 1991 *Current Protocols in Immunology* 1 (2): Chapter 5.

In general, such screening procedures involve providing appropriate cells which express a receptor polypeptide of the present invention on the surface thereof. Such cells include cells from mammals, insects, yeast, and bacteria. In particular, a polynucleotide encoding the receptor of the present invention is employed to transfect cells to thereby express a PTC taste receptor. The expressed receptor is then contacted with a test compound to observe binding, stimulation or inhibition of a functional response.

One such screening procedure involves the use of melanophores that are transfected to express a PTC taste receptor. Such a screening technique is described in PCT WO 92/01810, published Feb. 6, 1992. Such an assay may be employed to screen for a compound which inhibits activation of a receptor of the present invention by contacting the melanophore cells which encode the receptor with both a receptor ligand, such as PTC, and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express a PTC taste receptor (for example, transfected CHO cells) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a PTC taste receptor in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of labeled ligand, such as PTC, to cells which have the receptor on the surface thereof, or cell membranes containing the receptor. Such a method involves transfecting a eukaryotic cell with a DNA encoding a PTC taste receptor such that the cell expresses the receptor on its surface, or using of eukaryotic cells that express the receptor of the present invention on their surface (or using a eukaryotic cell that expresses the receptor on its surface). The cell is then contacted with a potential antagonist in the presence of a labeled form of a ligand, such as PTC. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand that binds to the receptors. This method is called a binding assay.

Another such screening procedure involves the use of eukaryotic cells, which are transfected to express the receptor of the present invention, or use of eukaryotic cells that express the receptor of the present invention on their surface. The cells are loaded with an indicator dye that produces a fluorescent signal when bound to calcium, and the cells are contacted with a test substance and a receptor agonist, such as PTC. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another such screening procedure involves use of eukaryotic cells, which are transfected to express the receptor of the present invention (or use of eukaryotic cells that express the receptor of the present invention), and which are also transfected with a reporter gene construct that is coupled to activation of the receptor (for example, luciferase or beta-galactosidase behind an appropriate promoter). The cells are contacted with a test substance and a receptor agonist, such as PTC, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another such screening technique for antagonists or agonists involves introducing RNA encoding a PTC taste receptor into *Xenopus* oocytes to transiently express the receptor. The receptor expressing oocytes are then contacted with a receptor ligand, such as PTC, and a compound to be screened. Inhibition or activation of the receptor is then determined by detection of a signal, such as, cAMP, calcium, proton, or other ions.

Another such technique of screening for antagonists or agonists involves determining inhibition or stimulation of PTC taste receptor-mediated cAMP and/or adenylate cyclase accumulation or diminution. Such a method involves transiently or stably transfecting a eukaryotic cell with a PTC taste receptor to express the receptor on the cell surface (or using a eukaryotic cell that expresses the receptor of the present invention on its surface). The cell is then exposed to potential antagonists in the presence of ligand, such as PTC. The amount of cAMP accumulation is then measured, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits PTC taste receptor binding, the levels of PTC taste receptor-mediated cAMP, or adenylate cyclase activity, will be reduced or increased.

Assays for Intracellular Proteins that Interact with the PTC Taste Receptor.

Any method suitable for detecting protein-protein interactions may be employed for identifying transmembrane proteins or intracellular proteins that interact with PTC taste receptor. Among the traditional methods which may be employed are co-immunoprecipitation, crosslinking and co-purification through gradients or chromatographic columns of cell lysates or proteins obtained from cell lysates and the PTC taste receptor to identify proteins in the lysate that interact with the PTC taste receptor. For these assays, the PTC taste receptor component used can be a full length PTC taste receptor, a soluble derivative lacking the membrane-anchoring region (e.g., a truncated PTC taste receptor in which all TMDs are deleted resulting in a truncated molecule containing ECDs fused to CDs), a peptide corresponding to a CD or a fusion protein containing a CD of PTC taste receptor. Once isolated, such an intracellular protein can be identified and can, in turn, be used, in conjunction with standard techniques, to identify proteins with which it interacts. For example, at least a portion of the amino acid sequence of an intracellular protein which interacts with the PTC taste receptor can be ascertained using techniques well known to those of skill in the art, such as via the Edman degradation technique. See, e.g., Creighton 1983 *Proteins: Structures and Molecular Principles*, W. H. Freeman & Co., N.Y., pp. 34-49. The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well known. See, e.g., Ausubel et al. 1989 *Current Protocols in Molecular Biology* Green Publishing Associates and Wiley Interscience, N.Y.; and Innis, M. et al., eds. 1990 *PCR Protocols: A Guide to Methods and Applications* Academic Press, Inc., New York.

Additionally, methods may be employed which result in the simultaneous identification of genes, which encode the transmembrane or intracellular proteins interacting with PTC taste receptor. These methods include, for example, probing expression libraries, in a manner similar to the well known technique of antibody probing of λgt11 libraries, using labeled PTC taste receptor protein, or a PTC taste receptor polypeptide, peptide or fusion protein, e.g., a PTC taste receptor polypeptide or PTC taste receptor domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al. 1991 *PNAS USA* 88:9578-9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a PTC taste receptor nucleotide sequence encoding PTC taste receptor, a PTC taste receptor polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, PTC taste receptor may be used as the bait gene product. Total genomic or cDNA sequences are fused to the DNA encoding an activation domain. This library and a plasmid encoding a hybrid of a bait PTC taste receptor gene product fused to the DNA-binding domain are cotransformed into a yeast reporter strain, and the resulting transformants are screened for those that express the reporter gene. For example, and not by way of limitation, a bait PTC taste receptor gene sequence, such as the open reading frame of PTC taste receptor (or a domain of PTC taste receptor) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait PTC taste receptor gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait PTC taste receptor gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait PTC taste receptor gene product will reconstitute an active GAL4 protein and thereby drive expression of the HIS3 gene. Colonies, which express HIS3, can be detected by their growth on petri dishes containing semi-solid agar based media lacking histidine. The cDNA can then be purified from these strains, and used to produce and isolate the bait PTC taste receptor gene-interacting protein using techniques routinely practiced in the art.

Assays for Compounds that Interfere with PTC Taste Receptor/Intracellular or PTC Taste Receptor/Transmembrane Macromolecule Interaction The macromolecules that interact with the PTC taste receptor are referred to, for purposes of this discussion, as "binding partners". These binding partners are likely to be involved in the PTC taste receptor signal transduction pathway, and therefore, in the role of PTC taste receptor in bitter tasting. Therefore, it is desirable to identify compounds that interfere with or disrupt the interaction of such binding partners with PTC taste receptor which may be useful in regulating the activity of the PTC taste receptor and control the sensitivity to bitter tastes associated with PTC taste receptor activity.

The basic principle of the assay systems used to identify compounds that interfere with the interaction between the PTC taste receptor and its binding partner or partners involves preparing a reaction mixture containing PTC taste receptor protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the PTC taste receptor moiety and its binding partner. Control reaction mixtures are incubated without the test compound or with a placebo. The formation of any complexes between the PTC taste receptor moiety and the binding partner is then detected. The formation of a complex in the control reaction, but not in the reaction mixture containing the test compound, indicates that the compound interferes with the interaction of the PTC taste receptor and the binding partner. Additionally, complex formation within reaction mixtures containing the test compound and the "wild-type" PTC taste receptor may also be compared to complex formation within reaction mixtures containing the test compound and the "mutant" PTC taste receptor. This comparison may be important in those cases wherein it is desirable to identify compounds that disrupt interactions of "wild-type" but not "mutant" PTC taste receptors.

The assay for compounds that interfere with the interaction of the PTC taste receptor and binding partners can be conducted in a heterogeneous or homogeneous format. Heterogeneous assays involve anchoring either the PTC taste receptor moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the PTC taste receptor moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the PTC taste receptor moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the PTC taste receptor gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes.

Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the PTC taste receptor moiety and the interactive binding partner is prepared in which either the PTC taste receptor or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances, which disrupt PTC taste receptor/intracellular binding partner interaction can be identified.

In a particular embodiment, a PTC taste receptor fusion can be prepared for immobilization. For example, the PTC taste receptor or a peptide fragment, e.g., corresponding to a CD, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-PTC taste receptor fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the PTC taste receptor gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-PTC taste receptor fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the PTC taste receptor/binding partner interaction can be detected by adding the labeled antibody and measuring the radioactivity associated with the beads.

In another embodiment of the invention, these same techniques can be employed using peptide fragments that correspond to the binding domains of the PTC taste receptor and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a PTC taste receptor gene product can be anchored to a solid material as described, above, by making a GST-PTC taste receptor fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored GST-PTC taste receptor fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

Assays for Identification of Compounds that Modulate Bitter Tastes

Compounds, including but not limited to compounds identified via assay techniques such as those described above, can be tested for the ability to modulate bitter tastes. The assays described above can identify compounds that affect PTC taste receptor activity (e.g., compounds that bind to the PTC taste receptor, inhibit binding of the natural ligand, and either activate signal transduction (agonists) or block activation (antagonists), and compounds that bind to the natural ligand of the PTC taste receptor and neutralize ligand activity); or compounds that affect PTC taste receptor gene activity (by affecting PTC taste receptor gene expression, including molecules, e.g., proteins or small organic molecules, that affect or interfere with events so that expression of the full length PTC taste receptor can be modulated). However, it should be noted that the assays described can also identify compounds that modulate PTC taste receptor signal transduction (e.g., compounds which affect downstream signalling events, such as inhibitors or enhancers of protein kinases or phosphatases activities which participate in transducing the signal activated by PTC binding to the PTC taste receptor). The identification and use of such compounds which affect another step in the PTC taste receptor signal transduction pathway in which the PTC taste receptor gene and/or PTC taste receptor gene product is involved and, by affecting this same pathway may modulate the effect of PTC taste receptor on the sensitivity to bitter tastes are within the scope of the invention. Such compounds can be used as part of a therapeutic method for modulating bitter tastes.

Cell-based systems, membrane vesicle-based systems and membrane fraction-based systems can be used to identify compounds that may act to modulate bitter tastes. Such cell systems can include, for example, recombinant or non-recombinant cells, such as cell lines, which express the PTC taste receptor gene. In addition, expression host cells (e.g., COS cells, CHO cells, HEK293 cells) genetically engineered to express a functional PTC taste receptor and to respond to activation by the natural ligand, e.g., as measured by a chemical or phenotypic change, induction of another host cell gene, change in ion flux (e.g., $Ca^{2+}$), phosphorylation of host cell proteins, etc., can be used as an end point in the assay.

In utilizing such cell systems, cells may be exposed to a compound suspected of exhibiting an ability to modulate bitter tastes, at a sufficient concentration and for a time sufficient to elicit such a modulation in the exposed cells.

After exposure, the cells can be assayed to measure alterations in the expression of the PTC taste receptor gene, e.g., by assaying cell lysates for PTC taste receptor mRNA transcripts (e.g., by Northern analysis) or for PTC taste receptor protein expressed in the cell; compounds which regulate or modulate expression of the PTC taste receptor gene are good candidates as therapeutics. Alternatively, the cells are examined to determine whether one or more cellular phenotypes has been altered to resemble a taster or nontaster type. Still further, the expression and/or activity of components of the signal transduction pathway of which PTC taste receptor is a part, or the activity of the PTC taste receptor signal transduction pathway itself can be assayed.

For example, after exposure, the cell lysates can be assayed for the presence of phosphorylation of host cell proteins, as compared to lysates derived from unexposed control cells. The ability of a test compound to inhibit phosphorylation of host cell proteins in these assay systems indicates that the test compound alters signal transduction initiated by PTC taste receptor activation. The cell lysates can be readily assayed using a Western blot format; i.e., the host cell proteins are resolved by gel electrophoresis, transferred and probed using a detection antibody (e.g., an antibody labeled with a signal generating compound, such as radiolabel, fluor, enzyme, etc.), see, e.g., Glenney et al. 1988 *J Immunol Methods* 109:277-285; Frackelton et al. 1983 *Mol Cell Biol* 3:1343-1352. Alternatively, an ELISA format could be used in which a particular host cell protein involved in the PTC taste receptor signal transduction pathway is immobilized using an anchoring antibody specific for the target host cell protein, and the presence or absence of a phosphorylated residue on the immobilized host cell protein is detected using a labeled antibody. (See, King et al. 1993 *Life Sci* 53:1465-1472). In yet another approach, ion flux, such as calcium ion flux, can be measured as an end point for PTC taste receptor stimulated signal transduction.

Other Assays for Modulators of PCT Taste Receptor

A. Assays for PTC Taste Receptor Protein Activity

PTC taste receptor family members are G-protein coupled receptors that participate in taste transduction, e.g., bitter taste transduction. The activity of PTC taste receptor polypeptides can be assessed using a variety of in vitro and in vivo assays to determine functional, chemical, and physical effects, e.g., measuring ligand binding (e.g., radioactive ligand binding), second messengers (e.g., cAMP, cGMP, IP3, DAG, or $Ca^{2+}$), ion flux, phosphorylation levels, transcription levels, neurotransmitter levels, and the like. Furthermore, such assays can be used to test for inhibitors and activators of PTC taste receptor family members. Modulators can also be genetically altered versions of PTC taste receptors. Such modulators of taste transduction activity are useful for customizing taste, for example to modify the detection of bitter tastes.

Modulators of PTC taste receptor activity are tested using PTC taste receptor polypeptides as described above, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation is tested using one of the in vitro or in vivo assays described herein. Taste transduction can also be examined in vitro with soluble or solid state reactions, using a full-length PTC taste receptor or a chimeric molecule such as an extracellular domain or transmembrane domain, or combination thereof, of a PTC taste receptor covalently linked to a heterologous signal transduction domain, or a heterologous extracellular domain and/or transmembrane domain covalently linked to the transmembrane and/or cytoplasmic domain of a PTC taste receptor. Furthermore, ligand-binding domains of the protein of interest can be used in vitro in soluble or solid state reactions to assay for ligand binding. In numerous embodiments, a chimeric receptor will be made that comprises all or part of a PTC taste receptor polypeptide as well an additional sequence that facilitates the localization of the PTC taste receptor to the membrane, such as a rhodopsin, e.g., an N-terminal fragment of a rhodopsin protein.

Ligand binding to a PTC taste receptor protein, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three known subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-G protein complex. In the presence of GTP, release of the known alpha subunit of the G protein from the other two known G protein subunits serves as a criterion of activation.

In a convenient embodiment, PTC taste receptor-gustducin interactions are monitored as a function of PTC taste receptor activation. One taste-cell specific G protein that has been identified is called gustducin (McLaughlin et al. 1992 *Nature* 357:563-569). Such ligand dependent coupling of PTC taste receptors with gustducin can be used as a marker to identify modifiers of the PTC taste receptor.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

In a convenient embodiment, a PTC taste receptor polypeptide is expressed in a eukaryotic cell as a chimeric receptor with a heterologous, chaperone sequence that facilitates its maturation and targeting through the secretory pathway. In a preferred embodiment, the heterologous sequence is a rhodopsin sequence, such as an N-terminal leader of a rhodopsin. Such chimeric PTC taste receptors can be expressed in any eukaryotic cell, such as HEK293 cells. Preferably, the cells comprise a functional G protein, e.g., Gα15, that is capable of coupling the chimeric receptor to an intracellular signaling pathway or to a signaling protein such as phospholipase Cβ. Activation of such chimeric receptors in such cells can be detected using any standard method, such as by detecting changes in intracellular calcium by detecting FURA-2 dependent fluorescence in the cell.

An activated G-protein coupled receptor (GPCR) becomes a substrate for kinases that phosphorylate the C-terminal tail of the receptor (and possibly other sites as well). Thus, activators will promote the transfer of $^{32}P$ from gamrnma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., Methods in Enzymology, vols. 237 and 238 (1994) and volume 96 (1983); Bourne et al. 1991 Nature 10:349:117-27; Bourne et al. 1990 Nature 348:125-32; Pitcher et al. 1998 Annu Rev Biochem 67:653-92.

Samples or assays that are treated with a potential PTC taste receptor protein inhibitor or activator are compared to control samples without the test compound, to examine the extent of modulation. Such assays may be carried out in the presence of a bitter tastant that is known to activate the particular receptor, and modulation of the bitter-tastant-dependent activation monitored. Control samples (untreated with activators or inhibitors) are assigned a relative PTC taste receptor activity value of 100. Inhibition of a PTC taste receptor protein is achieved when the PTC taste receptor activity value relative to the control is about 90%, optionally 50%, optionally 25-0%. Activation of a PTC taste receptor protein is achieved when the PTC taste receptor activity value relative to the control is 110%, optionally 150%, 200-500%, or 1000-2000%.

Changes in ion flux may be assessed by determining changes in polarization (i.e., electrical potential) of the cell or membrane expressing a PTC taste receptor protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al. 1997 New Engl J Med 336:1575-1595). Whole cell currents are conveniently determined using the standard methodology (see, e.g., Hamil et al. 1981 Pflugers Archiv 391:85). Other known assays include: radiolabeled ion flux assays and fluorescence assays using voltage-sensitive dyes (see, e.g., Vestergarrd-Bogind et al. 1988 J Membrane Biol 88:67-75; Gonzales & Tsien 1997 Chem Biol 4:269-277; Daniel et al. 1991 J Pharmacol Meth 25:185-193; Holevinsky et al. 1994 J Membrane Biology 137:59-70). Generally, the compounds to be tested are present in the range from 1 µM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Convenient assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al. 1991 PNAS USA 88:10049-10053). Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine 1984 Nature 312:315-21). EP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al. 1991 PNAS USA 88:9868-9872; and Dhallan et al. 1990 Nature 347:184-187). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a convenient embodiment, PTC taste receptor protein activity is measured by expressing a PTC taste receptor gene in a heterologous cell with a promiscuous G-protein that links the receptor to a phospholipase C signal transduction pathway (see Offermanns & Simon 1995 J Biol Chem 270:15175-15180). Optionally the cell line is HEK293 (which does not naturally express PTC taste receptor genes and the promiscuous G-protein is $G\alpha15$ (Offermanns & Simon, supra). Modulation of taste transduction is assayed by measuring changes in intracellular $Ca^{2+}$ levels, which change in response to modulation of the PTC taste receptor signal transduction pathway via administration of a molecule that associates with a PTC taste receptor protein. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon 1995 J Biol Chem 270: 15175-15180 may be used to determine the level of cAMP. Also, the method described in Felley-Bosco et al. 1994 Am J Resp Cell and Mol Biol 11:159-164 may be used to determine the level of cGMP. Further, an assay kit for measuring cAMP and/or cGMP is described in U.S. Pat. No. 4,115,538.

In another embodiment, phosphatidyl inositol (PI) hydrolysis can be analyzed according to U.S. Pat. No. 5,436,128. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing a PTC taste receptor protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128. The reporter genes can be, e.g., chloramphenicol acetyltransferase, luciferase, β-galactosidase and alkaline phosphatase. Furthermore, the protein of interest can be used as an indirect reporter via attachment to a second reporter such as green fluorescent protein (see, e.g., Mistili & Spector 1997 Nature Biotechnology 15:961-964).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of a PTC taste receptor family member can be any small chemical compound, or a biological entity, such as a protein, sugar, nucleic acid or lipid. Alternatively, modulators can be genetically altered versions of a PTC taste receptor gene. Typically, test compounds will be small chemical molecules and peptides. Essentially any chemical compound can be used as a potential modulator or ligand in the assays of the invention, although most often compounds dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one convenient embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particularly chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka 1991 Int J Pept Prot Res 37:487-493 and Houghton et al. 1991 Nature 354:84-88). Other chemistries for generating chemical diversity libraries can also be used. Such chemistries include, but are not limited to: peptides (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al. 1993 PNAS USA 90:6909-6913), vinylogous polypeptides (Hagihara et al. 1992 J Amer Chem Soc 114:6568), nonpeptidal peptidomimetics with glucose scaffolding (Hirschmann et al. 1992 J Amer Chem Soc 114:9217-9218), analogous organic syntheses of small compound libraries (Chen et al. 1994 J Amer Chem Soc 116:2661), oligocarbamates (Cho et al. 1993 Science 261:1303), and/or peptidyl phosphonates (Campbell et al. 1994 J Org Chem 59:658), nucleic acid libraries (see Sambrook et al. 1989 Molecular Cloning, A Laboratory Manual, Cold Springs Harbor Press, N.Y.; and Ausubel et al. 1989 Current Protocols in Molecular Biology Green Publishing Associates and Wiley Interscience, N.Y.), peptide nucleic acid libraries (see, e.g., U.S. Pat. No. 5,539,083), antibody libraries (see, e.g., Vaughn et al. 1996 Nature Biotechnology 14:309-314 and PCT/US96/10287), carbohydrate libraries (see, e.g., Liang et al. 1996 Science 274:1520-1522 and U.S. Pat. No. 5,593,853), small organic molecule libraries (see, e.g., benzodiazepines, Baum 1993 C&EN, Jan 18, page 33; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

C. Solid State and Soluble High Throughput Assays

In one embodiment the invention provide soluble assays using molecules such as a domain such as a ligand binding domain, an extracellular domain, a transmembrane domain, a transmembrane domain and a cytoplasmic domain, an active site, a subunit association region, etc.; a domain that is covalently linked to a heterologous protein to create a chimeric molecule; a PTC taste receptor protein; or a cell or tissue expressing a PTC taste receptor protein, either naturally occurring or recombinant. In another embodiment, the invention provides solid phase based in vitro assays in a high throughput format, where the domain, chimeric molecule, PTC taste receptor protein, or cell or tissue expressing the PTC taste receptor is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis, Mo.

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, viral receptor ligands, cytokine receptors, chemokine receptors, interleukin receptors, immunoglobulin receptors and antibodies, the cadherein family, the integrin family, the selectin family, and the like; (see, e.g., Pigott & Power 1993 *The Adhesion Molecule Facts Book I*). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield 1963 *J Am Chem Soc* 85:2149-2154 (describing solid phase synthesis of, e.g., peptides); Geysen et al. 1987 *J Immun Meth* 102:259-274 (describing synthesis of solid phase components on pins); Frank & Doring 1988 *Tetrahedron* 44:6031-6040 (describing synthesis of various peptide sequences on cellulose disks); Fodor et al. 1991 *Science* 251:767-777; Sheldon et al. 1993 *Clinical Chemistry* 39:718-719; and Kozal et al. 1996 *Nature Medicine* 2:753759 (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate PTC taste receptor protein activity involves computer assisted drug design, in which a computer system is used to generate a three-dimensional structure of a PTC taste receptor protein based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a PTC taste receptor polypeptide into the computer system. The nucleotide sequence encoding the polypeptide, or the amino acid sequence thereof, can be any of the "wild-type" and "mutant" PTC taste receptor. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Walls potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variable along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been granted, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the PTC taste receptor protein to identify ligands that bind to the protein. Binding affinity between the protein and ligands is determined using energy terms to determine which ligands have an enhanced probability of binding to the protein.

Pharmaceutical Preparations and Methods of Administration

Taste modulators can be administered directly to the mammalian subject for modulation of taste, e.g., modulation of bitter taste, in vivo. Administration is by any of the routes normally used for introducing a modulator compound into ultimate contact with the tissue to be treated, optionally the tongue or mouth. The taste modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally. The formulations of compounds can be presented in unit-dose or multi-dose sealed containers, such as ampules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound in a particular subject.

In determining the effective amounts of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the $LD_{50}$ of the modulator, and the side effects of the inhibitor at various concentrations, as applied to the mass and overall health of the subject. Administration can be accomplished via single or divided doses.

EXAMPLE 1

The inability to taste phenylthiocarbamide (PTC) is among the best-studied inherited traits in humans, although genetic studies of this trait have produced conflicting results. Using a quantitative measure of PTC sensitivity in the Utah C.E.P.H. reference families, we have identified a number of loci which specify non-taster status. A subset of families shows clear Mendelian inheritance and linkage to markers on chromosome 7q35. High resolution SNP genotyping across this region revealed significant allelic excess in non-tasters across a 250 kb region. A specific haplotype occurs in affected individuals in all 7q-linked families and in approximately 85% of unrelated non-taster individuals. The minimal shared haplotype spans 28 kb and this region contains one gene, a member of the G protein-coupled T2R bitter receptor family. Under a stringent quantitative definition of affection status, 95% of all non-tasters were homozygous for a single base substitution in this gene. This substitution encodes an alanine in place of the normal proline at amino acid 49, in the predicted first intracellular loop of this 7 transmembrane domain receptor. The frequency of this variant across the full range of PTC sensitivities suggests this allele serves as the major quantitative trait locus (QTL) for this phenotype. Primate studies and haplotype analysis of populations worldwide indicate this mutation is of ancient origin, preceding the divergence of Asian from European lineages in modern humans. The pro⇒ala mutation also exists uncommonly on another haplotype in Eurasians, while this mutation occurs on a unique haplotype in a large fraction of non-tasters from sub-Saharan African populations.

Since its discovery in 1931, the inability to taste PTC has been one of the most widely studied inherited traits in humans. While numerous early studies indicated that non-taster status is inherited in a simple recessive fashion, subsequent studies indicated more complex inheritance, and linkage studies have produced conflicting results. We performed linkage studies in 28 Utah C.E.P.H. families and demonstrated strong evidence for linkage to markers on chromosome 7q35, with additional significant evidence for markers on chromosomes 16p. Families showing linkage to 7q demonstrated clear Mendelian recessive transmission of the non-taster trait, and meiotic recombination events in these families revealed a 4 Mb region in which this gene resides. We have performed additional genotyping in these families and further refined this interval to 2.8 megabases. We have performed extensive analysis in this region, including high-resolution SNP haplotyping, bioinformatics, and comparative DNA sequencing.

The Utah C.E.P.H. families were enrolled in conjunction with the Utah Genetic Reference Project under University of Utah IRB approved protocol #410. Other subjects were enrolled under NIH/NINDS IRB approved protocol # DC-01-230. Phenotype determination was performed with a variation of the classical method (Kalmus, H. 1958 Ann Hum Genet 22:222-230), including a quinine threshold measurement to identify and exclude individuals with general bitter aguesia. DNA from unrelated individuals of known taster status was purified from peripheral blood by standard methods, and Human Diversity and primate DNAs were obtained from the Coriell Cell Repository. Genotyping of short tandem repeat polymorphism (STRP) markers was performed on an ABI 377 using standard Genotyper software, and genotyping of SNPs was performed by DNA sequencing in both directions using an ABI 377 with standard fluorescent methods.

Bioinformatics analysis was performed with the NCBI Human Genome databases and the Celera Discovery System. Gene finding was performed with BLASTX, and Gene Machine (GENESCAN and FGENES) software (GeneMachine, Division of Intramural Research, ), SNPs were developed using the NIH SNP database, DNA sequence comparisons were done using PHRED/PHRAP/CONSED software suite (Ewing B. et al. 1998 Genome Research 8:175-185; Gordon D. et al. 1998 Genome Research 8:195-202).

Haplotypes within the PTC-4 gene were determined by performing genomic PCR to obtain a single approximately 1000 bp product containing all 3 variant sites, followed by cloning of the mass product into TopoTA vector (Clonetech), and picking single colonies, which contained a single amplified haplotype.

Evaluation of allele excess was performed by Chi-square tests using Yates correction for continuity, and $P_{excess}$ values were calculated as previously described (Feder et al. 1996 Nature Genet 13:399-408), with curve-smoothing performed in Mathematica averaging each 3 successive values.

Refining the PTC Interval in Families.

Genotyping in chromosome 7-linked families using STRP markers at 7q35 revealed that the gene resides within an interval bounded by D7S2202 on the centromeric side and D7S661 on the telomeric side, at 149.9 cM and 155.1 cM respectively on the Marshfield genetic linkage map. This interval contains the KEL blood group antigen gene, consistent with previous linkage results. Additional genotyping in chromosome 7-linked families identified a smaller interval, bounded by SNPs at 145,003,957 bp. on the centromeric side and at ~147,872,000 bp. on the telomeric side, a 2.8 Mb region. In addition to the KEL antigen gene, this smaller interval contains 60 known or predicted genes. Thirty of these genes encode immunoglobulins, 7 are known or putative odorant receptor (OR) genes, and 6 are known or putative members of the T2R family of mammalian bitter taste receptors. All OR genes and T2R receptor genes (which are comprised of a single coding exon) were sequenced in taster and non-taster individuals in families showing linkage to chromosome 7q, and numerous sequence variants were observed. These sequence variants were all single nucleotide differences, and thus they served as useful SNP's for additional analysis of this region.

SNP Genotyping in Families and Unrelated Individuals.

Figure 6A:
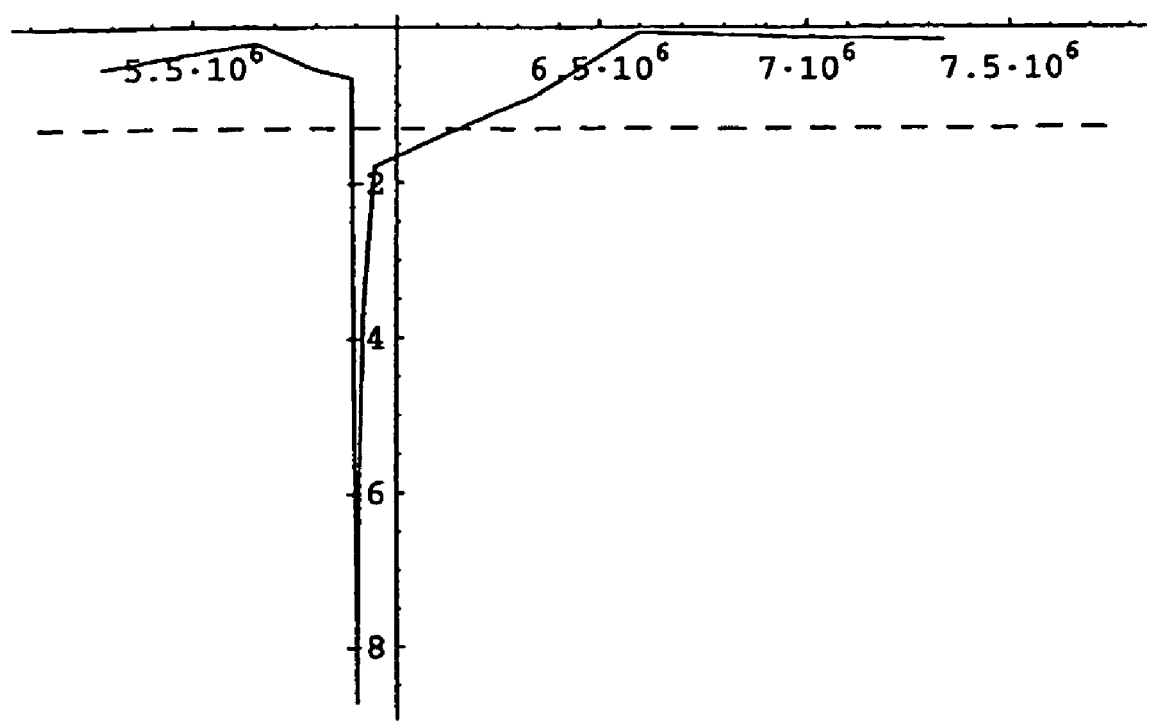
FIG. 6A shows statistical significance of allelic association across the chromosome 7 region. Chi-square p values comparing SNP allele frequencies in 23 unrelated non-tasters with the frequencies in 23 unrelated tasters, calculated using 1 degree of freedom and Yates correction for continuity. X axis: p values $\log_{10}$ scale, Y axis: physical location on chromosome 7q; location in base pairs, +140 million according to NCBI genome database as of March, 2002. For example, location $6.5 \times 10^6 = 146,500,000$ base pairs from pter. Plot smoothed using a rolling average of each 3 successive data points. Dotted line indicates significance level p=0.05. A sharp peak of significance, $p<10^{-8}$, occurs at 149,900,000 base pairs, the location of the PTC gene.
Figure 6B:
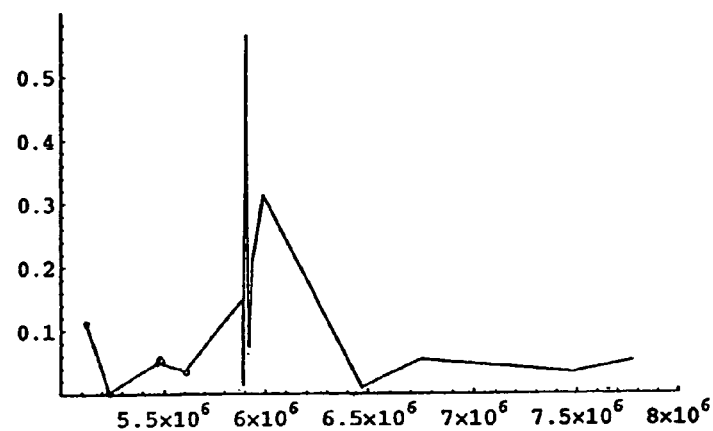
FIG. 6B shows allelic excess across the chromosome 7 region. X axis: allelic excess=frequency of the non-taster-associated allele in non-tasters minus its frequency in tasters, Y axis: physical location on chromosome 7q; location in base pairs, +140 million according to NCBI genome database as of March, 2002. For example, location $6.5 \times 10^6 = 146,500,000$ base pairs from pter, plot unsmoothed. Peak of allelic excess observed at 145,900,000 base pairs, the location of the PTC gene.

Comparison of these SNP's in affected and unaffected family members suggested that specific SNP alleles in a small portion of this region displayed an increase in frequency in affected compared to unaffected individuals. Additional SNPs at 100 kb intervals across the entire 2.8 Mb were developed and typed in chromosome 7-linked families, and also in a panel of 94 unrelated individuals of known PTC threshold. These genotypes were analyzed with respect to allele frequencies, and the results of this analysis are shown in FIG. 6A. SNP allele frequencies across a region of approximately 250 kb, extending from 145,900,000 to 146, 150,000 bp. displays Chi-square p values <0.05, with maximal significance ($p<10^{-9}$) occurring near the centromeric limit of this 250 kb region. Thus, markers in this region display strikingly different allele frequencies in non-tasters compared to tasters. In addition, $P_{excess}$ calculations were performed for each of these markers, comparing allele frequency in non-taster individuals to the frequency in taster individuals (FIG. 6B). While markers across most of the 2.8 Mb region showed low levels of allele excess ($\leq 0.1$), markers in the region from 145,900,000 to 146,800,000 bp. demonstrated elevated levels, with a sharp peak reaching approximately 0.5 near the centromeric side of this interval. These data suggest that a high proportion of all non-taster individuals share identity by descent for the chromosomal region near 145,900,000 bp., consistent with a strong founder effect for the non-taster variant.

Haplotype Analysis.

Haplotypes in this region were determined where possible for all individuals. The unambiguous haplotypes are shown in FIG. 7, which shows haplotypes across a 120 kb region for 94 unrelated individuals, listed in order of increasing sensitivity to PTC. When non-taster status is defined as PTC threshold $\leq 6.0$, all but seven non-tasters share a 3-SNP haplotype across a 741 bp region (G at 55,283, T at 55,923, and A at 56,024 in BAC RP11-707F14, AC073647.9). In addition, non-tasters share alleles extending in both directions; the mean shared genomic region was 61 kb. The highest allele sharing observed is at the SNP at position 55,283. At this position, 95% of all non-tasters in this sample are homozygous G, while 83/88 tasters carry one or more copies of the C allele. The minimum region shared by all non-tasters who carry the GTA haplotype extends from 42,445 bp to 71, 031 bp, a distance of 28,586 bp.

Gene Analysis and Segregation Studies.

Within this 28,586 bp region, database searches and gene prediction programs revealed only one apparent gene. This gene, which we designate PTC-4, encodes a novel member of the T2R bitter taste receptor family. The SNPs which give rise to the GTA haplotype all reside within the coding region of PTC-4. The T(55,923) encodes a valine in place of the alternative alanine, and the A(56,024) encodes an isoleucine in place of the alternative valine. Both of these SNPs failed to segregate absolutely with the PTC taste phenotype in the Utah families. In contrast, the G(55,283) which encodes an alanine in place of the alternative proline segregated absolutely with the phenotypes in the Utah families. Thirteen additional candidate genes in the 2.8 Mb region (6 T2R bitter receptor genes and 7 odorant receptor genes) were also fully sequenced in taster and non-taster individuals. All of these genes reside outside of the region of shared haplotype, and while sequence variation in these genes was observed, none segregated uniformly with the taster or non-taster phenotype.

The PTC-4 Gene.

As shown in FIGS. 1 and 2, the PTC-4 gene is 1002 bp, in length, encoding 333 amino acids. Hydropathy profile analysis predicts 7 transmembrane domains, typical of this class of G protein-coupled receptors (FIG. 3). It displays 30% amino acid identity to human T2RN, a prototype of a class of G protein-coupled receptors (GPCRs) known to act as bitter taste receptors in mammals. It appears to be unique among the mammalian T2R receptors to date in that its first extracellular domain is predicted to be 16 amino acids, more than twice as long as the 7 amino acids which constitute this domain in other family members (FIG. 4). The pro/ala variation occurs at amino acid 49, in the predicted first intracellular loop, adjacent to the second transmembrane domain.

Taster/Non-Taster Analyses.

While approximately 95% of all non-tasters are homozygous for the G/alanine variant of PTC-4, not all of these individuals share the GTA haplotype. For example, individuals K19-1, 72, K26-1, K27-1 and 39 in FIG. 7 carry the G on other haplotypes, and analysis of all haplotypes shows 7/37 G/G homozygotes fail to carry the T(55,923) and A(56,024) in homozygous form. Thus we estimate that the proportion of all non-tasters who descend from the major common ancestor is approximately 91%. Overall, the frequency of the G/alanine allele in our sample was 0.53. Assuming homozygosity for this allele is the sole cause of the non-taster phenotype, under Hardy-Weinberg equilibrium this would predict a non-taster frequency of 0.28, which approximates the frequency observed in the North American population.

Primate Studies Indicate G/ala is the Mutant Form.

Due to the high frequency of the G/ala allele in the population, we sought to determine which allele of PTC-4 represents the original form of the gene. We sequenced the PTC-4 gene in 6 primate species, humans and one individual each from chimpanzee, lowland gorilla, orangutan, crab-eating macaque (an old world monkey), and black-handed spider monkey (a new world monkey), representing over 25 million years of evolutionary divergence. All of the non-human primates were homozygous for the C/proline form, indicating that the G/alanine form is a mutation that arose in humans after the time they diverged from the nearest common primate ancestors.

Worldwide Distribution.

We performed genotyping of the G(55,283), T(55,923) and A(56,024) SNPs in DNAs from populations around the world, and the results are listed in Table 1. Approximately 46% of all haplotypes are the non-taster-associated GTA and an additional 49% are the taster-associated haplotype CCG. The GTA haplotype was observed in all Eurasian populations, but it was absent in Native Americans, who were exclusively homozygous for the CCG haplotype. In addition, the G/ala variant was observed on two other haplotypes, GCG, observed on approximately 2% of the mutant chromosomes, and GCA, observed on approximately 2%. The GCA haplotype was observed only in individuals of sub-Saharan African ancestry, suggesting that this haplotype carries a recurrence of the same mutation in Africa that has not undergone subsequent worldwide spread.

Analysis of QTL Contribution.

Our results combined with previous linkage analyses suggest PTC sensitivity is determined by several quantitative trait loci (QTLs). While this mutation underlies the majority of non-taster status in humans, other loci also affect this phenotype, as demonstrated by genome-wide linkage studies and by our observation of several tasters who are homozygous for the G/ala variant. Additional sequencing of the PTC-4 gene in these individuals showed no other sequence differences. These data support the view that chromosome 7q and other non-taster loci act epistatically at QTLs to determine an individual's overall PTC sensitivity threshold.

TABLE 1

Haplotype frequencies of the PTC gene in the world population

| | FREQUENCIES AMONG POPULATIONS | | | | | | |
|---|---|---|---|---|---|---|---|
| HAPLOTYPES | European | American Indian | African-American | Chinese | Korean | Japanese | Parkistanian |
| G-T-A | 0.47 | | 0.25 | 0.12 | 0.71 | 0.20 | 0.67 |
| G-C-G | 0.03 | | 0.04 | | | | |
| G-C-A | | | 0.17 | | | | |
| C-C-G | 0.49 | 1.00 | 0.50 | 0.88 | 0.29 | 0.80 | 0.33 |
| C-T-A | | | 0.04 | | | | |

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated PTC taste receptor polypeptide wherein the amino acid sequence of the polypeptide comprises the sequence shown in SEQ ID NO: 2 or SEQ ID NO: 4.

2. An isolated nucleic acid molecule encoding a chimeric protein comprising the PTC taste receptor polypeptide of claim 1 fused to a heterologous polypeptide.

3. A nucleotide vector comprising the isolated nucleic acid molecule of claim 2.

4. An expression vector comprising the isolated nucleic acid molecule of claim 2 in operative association with a nucleotide regulatory sequence that controls expression of the nucleic acid molecule in a host cell.

5. A genetically engineered host cell that comprises the isolated nucleic acid molecule of claim 2.

6. A chimeric protein comprising the polypeptide of claim 1 fused to a heterologous polypeptide.

7. An isolated polypeptide comprising SEQ ID NO: 2 or 4.

8. An isolated PTC taste receptor polypeptide which is an allelic variant of SEQ ID NO: 2, wherein the variant is selected from the group consisting of:
   the allelic variant where the amino acid at position 49 is an alanine, the amino acid at position 262 is an alanine and the amino acid at position 296 is an isoleucine;
   the allelic variant where the amino acid at position 49 is an alanine, the amino acid at position 262 is an alanine and the amino acid at position 296 is a valine;
   the allelic variant where the amino acid at position 49 is a proline; the amino acid at position 262 is an valine and the amino acid at position 296 is an isoleucine;
   the allelic variant where the amino acid at position 49 is a proline; the amino acid at position 262 is an alanine and the amino acid at position 296 is an isoleucine; and
   the allelic variant where the amino acid at position 49 is a proline; the amino acid at position 262 is an alanine and the amino acid at position 296 is a valine.

9. A chimeric protein comprising the polypeptide of claim 8 fused to a heterologous polypeptide.

10. An isolated nucleic acid molecule encoding a PTC taste receptor, wherein the nucleotide sequence of the nucleic acid molecule comprises the nucleotide sequence shown in SEQ ID NO: 1 or SEQ ID NO: 3.

11. A nucleotide vector comprising the isolated nucleic acid molecule of claim 10.

12. An expression vector comprising the isolated nucleic acid molecule of claim 10 in operative association with a nucleotide regulatory sequence that controls expression of the nucleic acid molecule in a host cell.

13. A genetically engineered host cell that comprises the isolated nucleic acid molecule of claim 10.

14. A method of making a PTC taste receptor, comprising,
culturing the host cell of claim 13 under conditions suitable for expression of said nucleic acid molecule encoding a PTC taste receptor and
recovering said PTC taste receptor from the cell culture.

15. The isolated nucleic acid molecule of claim 10, wherein the PTC taste receptor serves as a sensor for bitter taste of phenylthiocarbamide (PTC).

16. An isolated nucleic acid molecule encoding a PTC taste receptor which is an allelic variant of SEQ ID NO: 1, wherein the variant is selected from the group consisting of:
the allelic variant where the nucleotide at position 145 is a G, the nucleotide at position 785 is a C, and the nucleotide at position 886 is an A;
the allelic variant where the nucleotide at position 145 is a G, the nucleotide at position 785 is a C, and the nucleotide at position 886 is a G;
the allelic variant where the nucleotide at position 145 is a C, the nucleotide at position 785 is a T, and the nucleotide at position 886 is an A;
the allelic variant where the nucleotide at position 145 is a C, the nucleotide at position 785 is a C, and the nucleotide at position 886 is an A; and
the allelic variant where the nucleotide at position 145 is a C, the nucleotide at position 785 is a C, and the nucleotide at position 886 is a G.

17. An isolated nucleic acid molecule encoding a chimeric protein comprising the polypeptide encoded by the isolated nucleic acid molecule of claim 16 fused to a heterologous polypeptide.

18. A nucleotide vector comprising the isolated nucleic acid molecule of claim 16.

19. An expression vector comprising the isolated nucleic acid molecule of claim 16 in operative association with a nucleotide regulatory sequence that controls expression of the nucleic acid molecule in a host cell.

20. A genetically engineered host cell that comprises the isolated nucleic acid molecule of claim 16.

21. A method of screening compounds useful for modulating bitter taste, comprising
(i) contacting the compound in vitro with a host cell or membrane thereof that expresses a PTC taste receptor encoded by an isolated nucleic acid molecule comprising the sequence of SEQ ID NO: 1 or comprising the sequence of an allelic variant of SEQ ID NO: 1, wherein the allelic variant is selected from the group consisting of (a) the allelic variant where the nucleotide at position 145 is a G, the nucleotide at position 785 is a C, and the nucleotide at position 886 is an A; (b) the allelic variant where the nucleotide at position 145 is a G, the nucleotide at position 785 is a C, and the nucleotide at position 886 is a G; (c) the allelic variant where the nucleotide at position 145 is a C, the nucleotide at position 785 is a T, and the nucleotide at position 886 is an A; (d) the allelic variant where the nucleotide at position 145 is a C, the nucleotide at position 785 is a C, and the nucleotide at position 886 is an A; and (e) the allelic variant where the nucleotide at position 145 is a C, the nucleotide at position 785 is a C, and the nucleotide at position 886 is a G; and
(ii) detecting a change in the expression of said nucleic acid molecule or a change in activity of a gene product of said nucleic acid molecule, or detecting binding of said compound to the gene product of said nucleic acid molecule, or detecting a change in the electrical activity of said host cell or a change in intracellular cAMP, cGMP, IP3, or $Ca^2$ of said host cell.

22. The method of claim 21 wherein the gene product of said nucleic acid molecule is fused to a sequence that facilitates localization to the cell membrane, wherein the sequence is at least 20 consecutive N terminal amino acids of a rhodopsin protein.

23. The method of claim 21 wherein the cell is a HEK293 cell.

24. The method of claim 21 wherein a change in intracellular $Ca^{2+}$ is detected by measuring a change in FURA-2 dependent fluorescence in the cell.

* * * * *

UNITED STATES PATENT AND TRADEMARK OFFICE
CERTIFICATE OF CORRECTION

PATENT NO. : 7,314,725 B2
APPLICATION NO. : 10/484525
DATED : January 1, 2008
INVENTOR(S) : Drayna et al.

It is certified that error appears in the above-identified patent and that said Letters Patent is hereby corrected as shown below:

On the title page, item [56]:
In U.S. Patent Documents:
"2002/0128433" should read --2002/0218433--

In Other Publications:
On Page 1, under Guo and Reed: "Huamn" should read --Human--
On Page 2, Column 1, line 9: "NM 176817" should read --NM_176817--
On Page 2, Column 1, line 23: "NCI" should read --NCBI--
On Page 2, Column 1, line 25: "NBCI" should read --NCBI--
On Page 2, Column 1, line 27: "NBCI" should read --NCBI--
On Page 2, Column 1, line 29: "NBCI" should read --NCBI--
On Page 2, Column 1, line 31: "NBCI" should read --NCBI--
On Page 2, Column 1, line 32: "NBCI" should read --NCBI--
On Page 2, Column 1, line 34: "NBCI" should read --NCBI--
On Page 2, Column 1, line 36: "NBCI" should read --NCBI--
On Page 2, Column 1, line 37: "NBCI" should read --NCBI--
On Page 2, Column 1, line 38: "NBCI" should read --NCBI--
On Page 2, Column 2, line 10: "underlying taste sensitivity trait locus underlying taste sensitivity" should read --trait locus underlying taste sensitivity--
On Page 2, Column 2, line 12: "perception human" should read --perception to human--

Column 4, line 57: "T1R5" should read --T1Rs--
Column 7, line 3: "Springs" should read --Spring--
Column 7, line 52: "Springs" should read --Spring--
Column 11, line 12: "Springs" should read --Spring--
Column 11, line 58: "EFI" should read --EF1--
Column 11, line 67: ",to the E. coli" should read --to, the E. coli--
Column 15, line 7: "the a functional" should read --to a functional--
Column 18, line 21: "CHARMm" should read --CHARMM--
Column 27, line 36: "PCT" should read --PTC--
Column 28, line 8: "as well an" should read --as well as an--
Column 28, line 67: "gamrnma-labeled" should read --gamma-labeled--
Column 29, line 44: "1 µM" should read --1pM--
Column 30, line 8: "intrac-ellular" should read --intra-cellular--
Column 30, line 14: "EP3" should read --IP3--
Column 32, line 45: "Springs" should read --Spring--
Column 33, line 4: "provide soluble" should read --provides soluble--
Column 34, line 36: "2:753759" should read --2:753-759--

UNITED STATES PATENT AND TRADEMARK OFFICE
CERTIFICATE OF CORRECTION

PATENT NO.         : 7,314,725 B2
APPLICATION NO.    : 10/484525
DATED              : January 1, 2008
INVENTOR(S)        : Drayna et al.

It is certified that error appears in the above-identified patent and that said Letters Patent is hereby corrected as shown below:

Column 35, line 27: "variable along" should read --variables along--
Column 37, line 43: "(Clonetech)" should read --(Clontech)--
Column 38, line 50: "71, 031" should read --71,031--
Column 40, line 45: "Parkinstanian" should read --Pakistanian--

In the Claims:
Column 58, line 58: "an valine" should read --a valine--
Column 60, line 33: "$Ca^{2}$" should read --$Ca^{2+}$--
Column 60, line 42: "intrac-ellular" should read --intra-cellular--

Signed and Sealed this

Twenty-third Day of September, 2008

JON W. DUDAS
*Director of the United States Patent and Trademark Office*

SEQUENCE LISTING

<160> NUMBER OF SEQ ID NOS: 11

<210> SEQ ID NO 1

-continued

```
<211> LENGTH: 1002
<212> TYPE: DNA
<213> ORGANISM: Homo Sapiens

<400> SEQUENCE: 1
atgttgactc taactcgcat ccgcactgtg tcctatgaag tcaggagtac atttctgttc      60
atttcagtcc tggagtttgc agtggggttt ctgaccaatg ccttcgtttt cttggtgaat     120
ttttgggatg tagtgaagag gcagccactg agcaacagtg attgtgtgct gctgtgtctc     180
agcatcagcc ggcttttcct gcatggactg ctgttcctga gtgctatcca gcttacccac     240
ttccagaagt tgagtgaacc actgaaccac agctaccaag ccatcatcat gctatggatg     300
attgcaaacc aagccaacct ctggcttgct gcctgcctca gcctgcttta ctgctccaag     360
ctcatccgtt tctctcacac cttcctgatc tgcttggcaa gctgggtctc aggaagatc      420
tcccagatgc tcctgggtat tattctttgc tcctgcatct gcactgtcct ctgtgtttgg     480
tgcttttta gcagacctca cttcacagtc acaactgtgc tattcatgaa taacaataca     540
aggctcaact ggcagattaa agatctcaat ttatttttatt cctttctctt ctgctatctg     600
tggtctgtgc ctccttttcct attgtttctg gtttcttctg ggatgctgac tgtctccctg     660
ggaaggcaca tgaggacaat gaaggtctat accagaaact ctcgtgaccc cagcctggag     720
gcccacatta aagccctcaa gtctcttgtc tccttttttct gcttctttgt gatatcatcc     780
tgtgctgcct tcatctctgt gcccctactg attctgtggc gcgacaaaat agggtgatg      840
gtttgtgttg ggataatggc agcttgtccc tctgggcatg cagccatcct gatctcaggc     900
aatgccaagt tgaggagagc tgtgatgacc attctgctct gggctcagag cagcctgaag     960
gtaagagccg accacaaggc agattcccgg acactgtgct ga                        1002

<210> SEQ ID NO 2
<211> LENGTH: 333
<212> TYPE: PRT
<213> ORGANISM: Homo Sapiens

<400> SEQUENCE: 2

Met Leu Thr Leu Thr Arg Ile Arg Thr Val Ser Tyr Glu Val Arg Ser
  1               5                  10                  15

Thr Phe Leu Phe Ile Ser Val Leu Glu Phe Ala Val Gly Phe Leu Thr
                 20                  25                  30

Asn Ala Phe Val Phe Leu Val Asn Phe Trp Asp Val Val Lys Arg Gln
             35                  40                  45

Pro Leu Ser Asn Ser Asp Cys Val Leu Leu Cys Ser Ile Ser Arg
         50                  55                  60

Leu Phe Leu His Gly Leu Leu Phe Leu Ser Ala Ile Gln Leu Thr His
 65                  70                  75                  80

Phe Gln Lys Leu Ser Glu Pro Leu Asn His Ser Tyr Gln Ala Ile Ile
                 85                  90                  95

Met Leu Trp Met Ile Ala Asn Gln Ala Asn Leu Trp Leu Ala Ala Cys
                100                 105                 110

Leu Ser Leu Leu Tyr Cys Ser Lys Leu Ile Arg Phe Ser His Thr Phe
            115                 120                 125

Leu Ile Cys Leu Ala Ser Trp Val Ser Arg Lys Ile Ser Gln Met Leu
        130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175
```

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Ala Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 3
<211> LENGTH: 1002
<212> TYPE: DNA
<213> ORGANISM: Homo Sapiens

<400> SEQUENCE: 3

| | | | | | |
|---|---|---|---|---|---|
| atgttgactc | taactcgcat | ccgcactgtg | tcctatgaag | tcaggagtac | atttctgttc | 60 |
| atttcagtcc | tggagtttgc | agtggggttt | ctgaccaatg | ccttcgtttt | cttggtgaat | 120 |
| ttttgggatg | tagtgaagag | gcaggcactg | agcaacagtg | attgtgtgct | gctgtgtctc | 180 |
| agcatcagcc | ggcttttcct | gcatggactg | ctgttcctga | gtgctatcca | gcttacccac | 240 |
| ttccagaagt | tgagtgaacc | actgaaccac | agctaccaag | ccatcatcat | gctatggatg | 300 |
| attgcaaacc | aagccaacct | ctggcttgct | gcctgcctca | gcctgcttta | ctgctccaag | 360 |
| ctcatccgtt | tctctcacac | cttcctgatc | tgcttggcaa | gctgggtctc | aggaagatc | 420 |
| tcccagatgc | tcctgggtat | tattctttgc | tcctgcatct | gcactgtcct | ctgtgtttgg | 480 |
| tgctttttta | gcagacctca | cttcacagtc | acaactgtgc | tattcatgaa | taacaataca | 540 |
| aggctcaact | ggcagattaa | agatctcaat | ttatttatt | cctttctctt | ctgctatctg | 600 |
| tggtctgtgc | ctccttttcct | attgtttctg | gtttcttctg | ggatgctgac | tgtctccctg | 660 |
| ggaaggcaca | tgaggacaat | gaaggtctat | accagaaact | ctcgtgaccc | cagcctggag | 720 |
| gcccacatta | aagccctcaa | gtctcttgtc | tccttttttct | gcttctttgt | gatatcatcc | 780 |
| tgtgctgcct | tcatctctgt | gccctactg | attctgtggc | gcgacaaaat | agggtgatg | 840 |
| gtttgtgttg | gataatggc | agcttgtccc | tctgggcatg | cagccatcct | gatctcaggc | 900 |
| aatgccaagt | tgaggagagc | tgtgatgacc | attctgctct | gggctcagag | cagcctgaag | 960 |
| gtaagagccg | accacaaggc | agattcccgg | acactgtgct | ga | | 1002 |

<210> SEQ ID NO 4
<211> LENGTH: 333
<212> TYPE: PRT
<213> ORGANISM: Homo Sapiens

<400> SEQUENCE: 4

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Lys Arg Gln
        35                  40                  45

Ala Leu Ser Asn Ser Asp Cys Val Leu Cys Leu Ser Ile Ser Arg
50                  55                  60

Leu Phe Leu His Gly Leu Leu Phe Leu Ser Ala Ile Gln Leu Thr His
65              70                  75                  80

Phe Gln Lys Leu Ser Glu Pro Leu Asn His Ser Tyr Gln Ala Ile Ile
            85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
    195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Cys Phe Phe
                245                 250                 255

Val Ile Ser Ser Cys Ala Ala Phe Ile Ser Val Pro Leu Leu Ile Leu
            260                 265                 270

Trp Arg Asp Lys Ile Gly Val Met Val Cys Val Gly Ile Met Ala Ala
            275                 280                 285

Cys Pro Ser Gly His Ala Ala Ile Leu Ile Ser Gly Asn Ala Lys Leu
        290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 5
<211> LENGTH: 299
<212> TYPE: PRT
<213> ORGANISM: Homo Sapiens

<400> SEQUENCE: 5

Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Asn Gly
            20                  25                  30

Ile Asp Leu Ile Lys His Arg Lys Met Ala Pro Leu Asp Leu Leu Leu
            35                  40                  45

Ser Cys Leu Ala Val Ser Arg Ile Phe Leu Gln Leu Phe Ile Phe Tyr
    50                  55                  60

Val Asn Val Ile Val Ile Phe Phe Ile Glu Phe Ile Met Cys Ser Ala
 65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
                100                 105                 110

Pro Leu Phe Ile Trp Leu Lys Met Arg Ile Ser Lys Leu Val Pro Trp
                115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
                180                 185                 190

Ala Val Leu Leu Ile Phe Ser Leu Gly Arg His Thr Arg Gln Met
    195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
                260                 265                 270

His Ser Leu Ile Leu Ile Leu Gly Asn Pro Lys Leu Lys Gln Asn Ala
    275                 280                 285

Lys Lys Phe Leu Leu His Ser Lys Cys Cys Gln
    290                 295

<210> SEQ ID NO 6
<211> LENGTH: 335
<212> TYPE: PRT
<213> ORGANISM: Rat

<400> SEQUENCE: 6

Met Met Glu Gly His Ile Leu Phe Phe Leu Val Val Met Val Gln
 1               5                  10                  15

Phe Val Thr Gly Val Leu Ala Asn Gly Leu Ile Val Val His Ala
                20                  25                  30

Ile Asp Leu Ile Met Trp Lys Lys Met Ala Pro Leu Asp Leu Leu Leu
                35                  40                  45

Phe Cys Leu Ala Thr Ser Arg Ile Ile Leu Gln Leu Cys Ile Leu Phe
    50                  55                  60

Ala Gln Leu Cys Leu Phe Ser Leu Val Arg His Thr Leu Phe Glu Asp
 65                  70                  75                  80

Asn Ile Thr Phe Val Phe Ile Ile Asn Glu Leu Ser Leu Trp Phe Ala
                85                  90                  95

Thr Trp Leu Gly Val Phe Tyr Cys Ala Lys Ile Ala Thr Ile Pro His
                100                 105                 110

Pro Leu Phe Leu Trp Leu Lys Met Arg Ile Ser Arg Leu Val Pro Trp
                115                 120                 125

-continued

```
Leu Ile Leu Gly Ser Val Leu Tyr Val Ile Thr Thr Phe Ile His
    130                 135                 140

Ser Arg Glu Thr Ser Ala Ile Leu Lys Pro Ile Phe Ile Ser Leu Phe
145                 150                 155                 160

Pro Lys Asn Ala Thr Gln Val Gly Thr Gly His Ala Thr Leu Leu Ser
                165                 170                 175

Val Leu Val Leu Gly Leu Thr Leu Pro Leu Phe Ile Phe Thr Val Ala
            180                 185                 190

Val Leu Leu Ile Tyr Ser Leu Trp Asn Tyr Ser Arg Gln Met Arg
        195                 200                 205

Thr Met Val Gly Thr Arg Glu Tyr Ser Gly His Ala His Ile Ser Ala
    210                 215                 220

Met Leu Ser Ile Leu Ser Phe Leu Ile Leu Tyr Leu Ser His Tyr Met
225                 230                 235                 240

Val Ala Val Leu Ile Ser Thr Gln Val Leu Tyr Leu Gly Ser Arg Thr
                245                 250                 255

Phe Val Phe Cys Leu Leu Val Ile Gly Met Tyr Pro Ser Ile His Ser
            260                 265                 270

Ile Val Leu Ile Leu Gly Asn Pro Lys Leu Lys Arg Asn Ala Lys Met
        275                 280                 285

Phe Ile Val His Cys Lys Cys His Cys Thr Arg Ala Trp Val Thr
    290                 295                 300

Ser Arg Ser Pro Arg Leu Ser Asp Leu Pro Val Pro Thr His Pro
305                 310                 315                 320

Ser Ala Asn Lys Thr Ser Cys Ser Glu Ala Cys Ile Met Pro Ser
                325                 330                 335

<210> SEQ ID NO 7
<211> LENGTH: 335
<212> TYPE: PRT
<213> ORGANISM: mouse

<400> SEQUENCE: 7

Met Met Glu Gly His Met Leu Phe Phe Leu Leu Val Val Val Gln
  1               5                  10                  15

Phe Leu Thr Gly Val Leu Ala Asn Gly Leu Ile Val Val Asn Ala
            20                  25                  30

Ile Asp Leu Ile Met Trp Lys Lys Met Ala Pro Leu Asp Leu Leu
        35                  40                  45

Phe Cys Leu Ala Thr Ser Arg Ile Ile Leu Gln Leu Cys Ile Leu Phe
 50                  55                  60

Ala Gln Leu Gly Leu Ser Cys Leu Val Arg His Thr Leu Phe Ala Asp
65                  70                  75                  80

Asn Val Thr Phe Val Tyr Ile Ile Asn Glu Leu Ser Leu Trp Phe Ala
                85                  90                  95

Thr Trp Leu Gly Val Phe Tyr Cys Ala Lys Ile Ala Thr Ile Pro His
            100                 105                 110

Pro Leu Phe Leu Trp Leu Lys Met Arg Ile Ser Arg Leu Val Pro Trp
        115                 120                 125

Leu Ile Leu Ala Ser Val Val Tyr Val Thr Val Thr Thr Phe Ile His
    130                 135                 140

Ser Arg Glu Thr Ser Glu Leu Pro Lys Gln Ile Phe Ile Ser Phe Phe
145                 150                 155                 160

Ser Lys Asn Thr Thr Arg Val Arg Pro Ala His Ala Thr Leu Leu Ser
                165                 170                 175
```

```
Val Phe Val Phe Gly Leu Thr Leu Pro Phe Leu Ile Phe Thr Val Ala
            180                 185                 190

Val Leu Leu Leu Leu Ser Ser Leu Trp Asn His Ser Arg Gln Met Arg
        195                 200                 205

Thr Met Val Gly Thr Arg Glu Pro Ser Arg His Ala Leu Val Ser Ala
    210                 215                 220

Met Leu Ser Ile Leu Ser Phe Leu Ile Leu Tyr Leu Ser His Asp Met
225                 230                 235                 240

Val Ala Val Leu Ile Cys Thr Gln Gly Leu His Phe Gly Ser Arg Thr
                245                 250                 255

Phe Ala Phe Cys Leu Leu Val Ile Gly Met Tyr Pro Ser Leu His Ser
            260                 265                 270

Ile Val Leu Ile Leu Gly Asn Pro Lys Leu Lys Arg Asn Ala Lys Thr
        275                 280                 285

Phe Ile Val His Cys Lys Cys His Cys Ala Arg Ala Trp Val Thr
    290                 295                 300

Ser Arg Asn Pro Arg Leu Ser Asp Leu Pro Val Pro Ala Thr His His
305                 310                 315                 320

Ser Ala Asn Lys Thr Ser Cys Ser Glu Ala Cys Ile Met Pro Ser
                325                 330                 335

<210> SEQ ID NO 8
<211> LENGTH: 316
<212> TYPE: PRT
<213> ORGANISM: Homo sapiens

<400> SEQUENCE: 8

Met Met Gly Leu Thr Glu Gly Val Phe Leu Ile Leu Ser Gly Thr Gln
  1               5                  10                  15

Phe Thr Leu Gly Ile Leu Val Asn Cys Phe Ile Glu Leu Val Asn Gly
                 20                  25                  30

Ser Ser Trp Phe Lys Thr Lys Arg Met Ser Leu Ser Asp Phe Ile Ile
             35                  40                  45

Thr Thr Leu Ala Leu Leu Arg Ile Ile Leu Leu Cys Ile Ile Leu Thr
         50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                 85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
    210                 215                 220
```

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
            245                 250                 255

Asn Phe Leu Pro Lys Thr Lys Met Ala Lys Met Ile Gly Glu Val Met
        260                 265                 270

Thr Met Phe Tyr Pro Ala Gly His Ser Phe Ile Leu Ile Leu Gly Asn
    275                 280                 285

Ser Lys Leu Lys Gln Thr Phe Val Val Met Leu Arg Cys Glu Ser Gly
290                 295                 300

His Leu Lys Pro Gly Ser Lys Gly Pro Ile Phe Ser
305                 310                 315

<210> SEQ ID NO 9
<211> LENGTH: 299
<212> TYPE: PRT
<213> ORGANISM: Homo Sapiens

<400> SEQUENCE: 9

Met Leu Arg Leu Phe Tyr Phe Ser Ala Ile Ala Ser Val Ile Leu
1               5                   10                  15

Asn Phe Val Gly Ile Ile Met Asn Leu Phe Ile Thr Val Val Asn Cys
                20                  25                  30

Lys Thr Trp Val Lys Ser His Arg Ile Ser Ser Asp Arg Ile Leu
            35                  40                  45

Phe Ser Leu Gly Ile Thr Arg Phe Leu Met Leu Gly Leu Phe Leu Val
50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
                100                 105                 110

Phe Gln His Ser Val Phe Leu Leu Leu Lys Arg Asn Ile Ser Pro Lys
            115                 120                 125

Ile Pro Arg Leu Leu Leu Ala Cys Val Leu Ile Ser Ala Phe Thr Thr
130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190

Val Thr Ser Ala Ser Leu Leu Ile His Ser Leu Arg Arg His Ile Gln
195                 200                 205

Lys Met Gln Lys Asn Ala Thr Gly Phe Trp Asn Pro Gln Thr Glu Ala
210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
            260                 265                 270

Ser Pro Gly His Ser Val Leu Ile Ile Thr His Pro Lys Leu Lys
275                 280                 285

Thr Thr Ala Lys Lys Ile Leu Cys Phe Lys Lys
            290                 295

<210> SEQ ID NO 10
<211> LENGTH: 297
<212> TYPE: PRT
<213> ORGANISM: mouse

<400> SEQUENCE: 10

Met Leu Trp Glu Leu Tyr Val Phe Val Phe Ala Ala Ser Val Phe Leu
  1               5                  10                  15

Asn Phe Val Gly Ile Ile Ala Asn Leu Phe Ile Ile Val Ile Ile Ile
                 20                  25                  30

Lys Thr Trp Val Asn Ser Arg Arg Ile Ala Ser Pro Asp Arg Ile Leu
             35                  40                  45

Phe Ser Leu Ala Ile Thr Arg Phe Leu Thr Leu Gly Leu Phe Leu Leu
         50                  55                  60

Asn Ser Val Tyr Ile Ala Thr Asn Thr Gly Arg Ser Val Tyr Phe Ser
 65                  70                  75                  80

Thr Phe Phe Leu Leu Cys Trp Lys Phe Leu Asp Ala Asn Ser Leu Trp
                 85                  90                  95

Leu Val Thr Ile Leu Asn Ser Leu Tyr Cys Val Lys Ile Thr Asn Phe
            100                 105                 110

Gln His Pro Val Phe Leu Leu Lys Arg Thr Ile Ser Met Lys Thr
        115                 120                 125

Thr Ser Leu Leu Leu Ala Cys Leu Leu Ile Ser Ala Leu Thr Thr Leu
    130                 135                 140

Leu Tyr Tyr Met Leu Ser Gln Ile Ser Arg Phe Pro Glu His Ile Ile
145                 150                 155                 160

Gly Arg Asn Asp Thr Ser Phe Asp Leu Ser Asp Gly Ile Leu Thr Leu
                165                 170                 175

Val Ala Ser Leu Val Leu Asn Ser Leu Leu Gln Phe Met Leu Asn Val
                180                 185                 190

Thr Phe Ala Ser Leu Leu Ile His Ser Leu Arg Arg His Ile Gln Lys
            195                 200                 205

Met Gln Arg Asn Arg Thr Ser Phe Trp Asn Pro Gln Thr Glu Ala His
    210                 215                 220

Met Gly Ala Met Arg Leu Met Ile Cys Phe Leu Val Leu Tyr Ile Pro
225                 230                 235                 240

Tyr Ser Ile Ala Thr Leu Leu Tyr Leu Pro Ser Tyr Met Arg Lys Asn
                245                 250                 255

Leu Arg Ala Gln Ala Ile Cys Met Ile Ile Thr Ala Ala Tyr Pro Pro
            260                 265                 270

Gly His Ser Val Leu Leu Ile Ile Thr His His Lys Leu Lys Ala Lys
        275                 280                 285

Ala Lys Lys Ile Phe Cys Phe Tyr Lys
    290                 295

<210> SEQ ID NO 11
<211> LENGTH: 299
<212> TYPE: PRT
<213> ORGANISM: Homo Sapiens

<400> SEQUENCE: 11

Met Leu Ser Ala Gly Leu Gly Leu Leu Met Leu Val Ala Val Val Glu
  1               5                  10                  15

```
Phe Leu Ile Gly Leu Ile Gly Asn Gly Ser Leu Val Val Trp Ser Phe
            20              25                  30
Arg Glu Trp Ile Arg Lys Phe Asn Trp Ser Ser Tyr Asn Leu Ile Ile
            35              40                  45
Leu Gly Leu Ala Gly Cys Arg Phe Leu Leu Gln Trp Leu Ile Ile Leu
            50              55                  60
Asp Leu Ser Leu Phe Pro Leu Phe Gln Ser Ser Arg Trp Leu Arg Tyr
 65              70              75                          80
Leu Ser Ile Phe Trp Val Leu Val Ser Gln Ala Ser Leu Trp Phe Ala
                85              90                      95
Thr Phe Leu Ser Val Phe Tyr Cys Lys Lys Ile Thr Thr Phe Asp Arg
            100             105                 110
Pro Ala Tyr Leu Trp Leu Lys Gln Arg Ala Tyr Asn Leu Ser Leu Trp
            115             120                 125
Cys Leu Leu Gly Tyr Phe Ile Ile Asn Leu Leu Leu Thr Val Gln Ile
    130             135                 140
Gly Leu Thr Phe Tyr His Pro Pro Gln Gly Asn Ser Ser Ile Arg Tyr
145             150             155                         160
Pro Phe Glu Ser Trp Gln Tyr Leu Tyr Ala Phe Gln Leu Asn Ser Gly
                165             170                 175
Ser Tyr Leu Pro Leu Val Val Phe Leu Val Ser Ser Gly Met Leu Ile
            180             185                 190
Val Ser Leu Tyr Thr His His Lys Lys Met Lys Val His Ser Ala Gly
        195             200                 205
Arg Arg Asp Val Arg Ala Lys Ala His Ile Thr Ala Leu Lys Ser Leu
        210             215                 220
Gly Cys Phe Leu Leu Leu His Leu Val Tyr Ile Met Ala Ser Pro Phe
225             230                 235                     240
Ser Ile Thr Ser Lys Thr Tyr Pro Pro Asp Leu Thr Ser Val Phe Ile
            245             250                 255
Trp Glu Thr Leu Met Ala Ala Tyr Pro Ser Leu His Ser Leu Ile Leu
            260             265                 270
Ile Met Gly Ile Pro Arg Val Lys Gln Thr Cys Gln Lys Ile Leu Trp
        275             280                 285
Lys Thr Val Cys Ala Arg Arg Cys Trp Gly Pro
290                 295
```